US009588132B2

(12) United States Patent
Hattori et al.

(10) Patent No.: US 9,588,132 B2
(45) Date of Patent: *Mar. 7, 2017

(54) VALIDATION METHOD FOR AUTOMATED ANALYZERS

(71) Applicants: Uniflex Company, Ltd., Tokyo (JP); Artel, Inc., Westbrook, ME (US)

(72) Inventors: Akira Hattori, Abiko (JP); George Rodrigues, Westbrook, ME (US); Axel Bjoern Carle, Portland, ME (US)

(73) Assignees: Artel, Inc., Westbrook, ME (US); Uniflex Company, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/588,974

(22) Filed: Jan. 4, 2015

(65) Prior Publication Data

US 2015/0112629 A1 Apr. 23, 2015

Related U.S. Application Data

(63) Continuation-in-part of application No. 13/439,861, filed on Apr. 5, 2012, now Pat. No. 8,928,884.

(30) Foreign Application Priority Data

Apr. 8, 2011 (JP) ................................. 2011-086354

(51) Int. Cl.
| | |
|---|---|
| G01N 21/00 | (2006.01) |
| G01N 35/10 | (2006.01) |
| G01F 25/00 | (2006.01) |
| G01N 21/59 | (2006.01) |
| G01N 35/00 | (2006.01) |
| G01N 21/25 | (2006.01) |
| G01N 21/78 | (2006.01) |

(52) U.S. Cl.
CPC ............. *G01N 35/10* (2013.01); *G01F 25/00* (2013.01); *G01N 21/253* (2013.01); *G01N 21/59* (2013.01); *G01N 35/00623* (2013.01); *G01N 35/1016* (2013.01); *G01N 21/78* (2013.01)

(58) Field of Classification Search
CPC ............... G01N 21/8507; G01N 21/31; G01N 21/0303; G01N 21/59; G01N 21/05
USPC ........................................ 356/436, 445, 128
See application file for complete search history.

(56) References Cited

U.S. PATENT DOCUMENTS

| | | | |
|---|---|---|---|
| 4,036,590 A * | 7/1977 | Helder | ................... G01N 21/78 422/81 |
| 5,298,978 A | 3/1994 | Curtis et al. | |
| 5,492,673 A | 2/1996 | Curtis et al. | |
| 5,501,984 A * | 3/1996 | Hofstetter | .......... G01N 35/1065 422/63 |
| 6,741,365 B2 | 5/2004 | Curtis | |
| 7,187,455 B2 | 3/2007 | Curtis | |
| 7,772,008 B2 | 8/2010 | Curtis et al. | |
| 7,791,716 B2 | 9/2010 | McNally et al. | |
| 7,919,327 B2 | 4/2011 | Bradshaw et al. | |
| 7,998,747 B2 | 8/2011 | Bradshaw et al. | |

(Continued)

*Primary Examiner* — Tarifur Chowdhury
*Assistant Examiner* — Isiaka Akanbi
(74) *Attorney, Agent, or Firm* — Caseiro Burke LLC; Chris A. Caseiro

(57) ABSTRACT

Method for validating the accuracy of automated analyzers by performing an improved dual dye ratio method procedure that uses at least first and second dye solutions in combination with gravimetric measurement of selected test solutions.

20 Claims, 12 Drawing Sheets

(56) References Cited

U.S. PATENT DOCUMENTS

| | | |
|---|---|---|
| 8,003,405 B2 | 8/2011 | Albert et al. |
| 8,404,158 B2 | 3/2013 | Curtis et al. |
| 8,542,362 B2 * | 9/2013 | Yeo ................... B01L 3/5027 356/433 |
| 2004/0156748 A1 | 8/2004 | Yamakawa et al. |
| 2006/0097155 A1 | 5/2006 | Adachi et al. |
| 2006/0166373 A1 | 7/2006 | Enoki et al. |
| 2007/0264156 A1 | 11/2007 | Yamakawa et al. |
| 2011/0110822 A1 | 5/2011 | Adachi et al. |

* cited by examiner

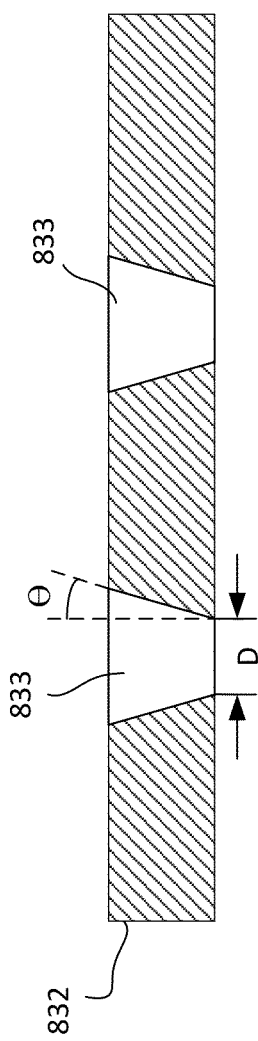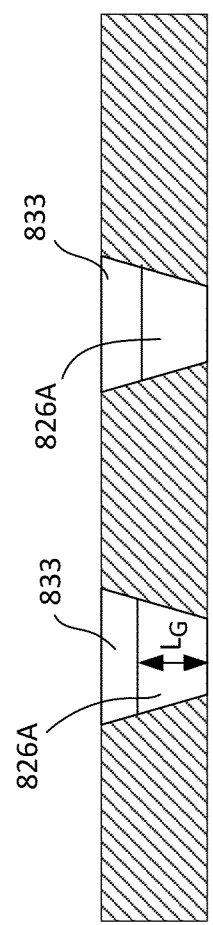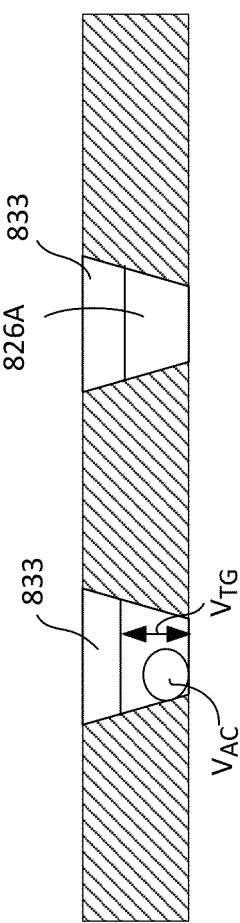
Figure 10A
Figure 10B
Figure 10C

VALIDATION METHOD FOR AUTOMATED ANALYZERS

CROSS-REFERENCE TO RELATED APPLICATIONS

This is a continuation-in-part application of co-pending U.S. patent application Ser. No. 13/439,861, filed on Apr. 5, 2012, which claims priority to Japanese Patent Application No. 2011-086354, filed on Apr. 8, 2011, the disclosures of which are herein incorporated by reference in their entireties.

BACKGROUND

Automated analyzers, including clinical biochemistry analyzers and other laboratory devices, have been conventionally used for many years. For example, automated clinical biochemistry analyzers are used to perform clinical testing on blood samples. These devices are required to produce results that are validated, and they must be calibrated, i.e., re-validated, on a regular basis.

Such analyzers have been calibrated using "standards" that are composed of the chemical substances present in test serums. However, the problems of accuracy of the calibration can arise, especially in terms of determining absolute values.

A method for improving the accuracy of the calibration can be accomplished by determining the differences between large numbers of test results using standards performed independently through blind studies conducted by several groups. Although this technique can be used universally, it is still inadequate for use as a method for confirming accuracy, because it is burdensome and time consuming.

In recent years, the certified accuracy of verification systems and devices has been determined by using analysis results obtained with a standard as true values based on a theoretical system for establishing the authenticity of world standards, and then determining accuracy by using trueness with respect thereto as a requirement for certification, and it is effective to realize validation techniques that coincide with these certification requirements.

In contrast, a validation technique has been previously proposed that improves calibration accuracy by reducing the effect of evaporation by dispensing an amount of liquid targeted for automated analysis (for example, 1 µl to 1000 µl) as determined according to a standard validation method from a liquid targeted for testing, and validating based on a dye method.

Validation techniques using dye methods consist of placing a prescribed amount of a reference solution containing a first dye component that absorbs light of a first wavelength in an absorbance detection container, measuring the optical absorbance of that wavelength component, placing a detection solution containing a second dye component that absorbs light of a second wavelength in the reference solution, and then measuring the optical absorbance of that wavelength component.

Since a comparison of the optical absorbance of the reference solution and the optical absorbance of the detection solution measured in this manner yields a value corresponding to the amount of the detection liquid, the amount of the detection liquid can be validated based on the amount of the reference liquid (based on the specifications of international standard—ISO8655—part 7).

Validation accuracy can be established for the elements used to determine accuracy of blood analysis results obtained by this dye method by firstly validating the light path length of the cell used for optical analyses, secondly validating the accuracy of dispensing of reaction reagents, thirdly validating the dispensing accuracy of biological specimens (blood), and fourthly validating incubation-temperature accuracy of the reaction layer.

SUMMARY

The embodiments generally relate to methods for validating and/or calibrating with a high degree of accuracy automated analyzers having liquid dispensers. The present methods for validating the accuracy of automated analyzers are directed to performing an improved dual dye ratio method validation procedure that uses first dye solution and second dye solution in a target test liquid, measuring at the weight of the second dye solution, performing a first and second optical analysis on the target test liquid, and performing a computational analysis that determines any deviation between and among the first and second optical analyses and the weight measurement for the second dye solution.

In one embodiment of the present method includes the steps of designating as a validation target an automated analyzer that sequentially carries out automated analyses by dispensing an automated analysis target liquid into a plurality of optical analysis cells by an analysis target liquid filling unit and sequentially filling a first dye solution (having red and blue dyes) dispensed from a first liquid holding unit into the plurality of optical analysis cells by using the analysis target liquid filling unit. Then, dispensing a second dye solution (having blue dye only) from a second liquid holding unit by using a diluent dispensing pipetter, and weighing, on the basis of a gravimetric method, a total weight of the diluent dispensing pipetter with the second dye solution (having blue dye only) using a diluent weighing unit, and pipetting the second dye solution (having blue dye only) into the optical analysis cells filled with the first dye solution (having red and blue dyes). Measuring a target liquid in the optical analysis cells comprising the first and second dye solutions by an optical absorbance detection unit, based on a dual dye ratio method, in order to determine the amount of liquid of the first dye solution as a target liquid volume measurement result, weighing, based on the gravimetric method, the diluent dispensing pipetter after pipetting the second dye solution by a pipetter weighing unit, and transferring the target liquid from the optical analysis cells to a reference value measurement unit (e.g., microplate and reader) by using a transfer pipetter and measuring, based on the dual dye ratio method, to determine by a second optical absorbance detection unit the amount of the first dye solution as a reference liquid volume measurement result. Finally, validating the dispensing accuracy of the analysis target liquid dispensing unit of the automated analyzer by computing any deviation between and among the reference liquid volume measurement result and the target liquid volume measurement result and the measurement results of the pipetter weighing unit and the diluent weighing unit determined based on the gravimetric method.

In another embodiment of the present method includes the steps of designating as a validation target an automated analyzer that sequentially carries out automated analyses by dispensing an automated analysis target liquid into a plurality of optical analysis cells by a first and second analysis target liquid filling units, and sequentially filling a first dye solution (having red and blue dyes) into the plurality of optical analysis cells by dispensing from a first liquid holding unit by using the first analysis target liquid filling unit. Then, dispensing a second dye solution (having blue dye only) from a second liquid holding unit by using a diluent dispensing pipette, and weighing the diluent dispensing pipetter with the second dye solution using a diluent weighing unit, and pipetting the second dye solution into the optical analysis cells filled with the first dye solution (having red and blue dyes). In addition, placing a third dye solution (having blue dye only) into the optical analysis cells containing the first and second dye solutions, dispensed from a third liquid holding unit, using the second analysis target liquid filling unit. Measuring a target liquid in the optical analysis cells comprising the first, second and third dye solutions by an optical absorbance detection unit, based on a dye method, to determine an amount of the first dye solution as a target liquid volume measurement result, and weighing the diluent dispensing pipetter after pipetting the second dye solution by a pipetter weighing unit, and transferring the target liquid from the optical analysis cells to a reference value measurement unit (e.g., microplate and reader) by using a transfer pipetter and measuring, based on the dual dye ratio method, to determine by a second optical absorbance detection unit the amount of the first dye solution as a reference liquid volume measurement result. Finally, validating the dispensing accuracy of the analysis target liquid dispensing unit of the automated analyzer by computing any deviation between and among the reference liquid volume measurement result and the target liquid volume measurement result and the measurement results of the pipetter weighing unit and the diluent weighing unit determined based on the gravimetric method.

According to the present method, the accuracy of validation results for an automated analyzer can be improved by determining the amount of a validation target liquid based on measurement of the amount of a reference liquid with respect to the amount of the validation target liquid based on measurement of a target liquid by a dual dye ratio method using first and second traceable dye solutions, using a target value measurement result according to a gravimetric method.

These and other objects, along with advantages and features of the present disclosure herein disclosed, will become apparent through reference to the following description and the accompanying drawings. Furthermore, it is understood that the features of the various embodiments described herein are not mutually exclusive and can exist in various combinations and permutations.

BRIEF DESCRIPTION OF THE DRAWINGS

FIGS. 10A-10C show an embodiment of a method to determine the actual dispensed volume of the dispensing pipette under test in a validation section.

DESCRIPTION

Figure 1:
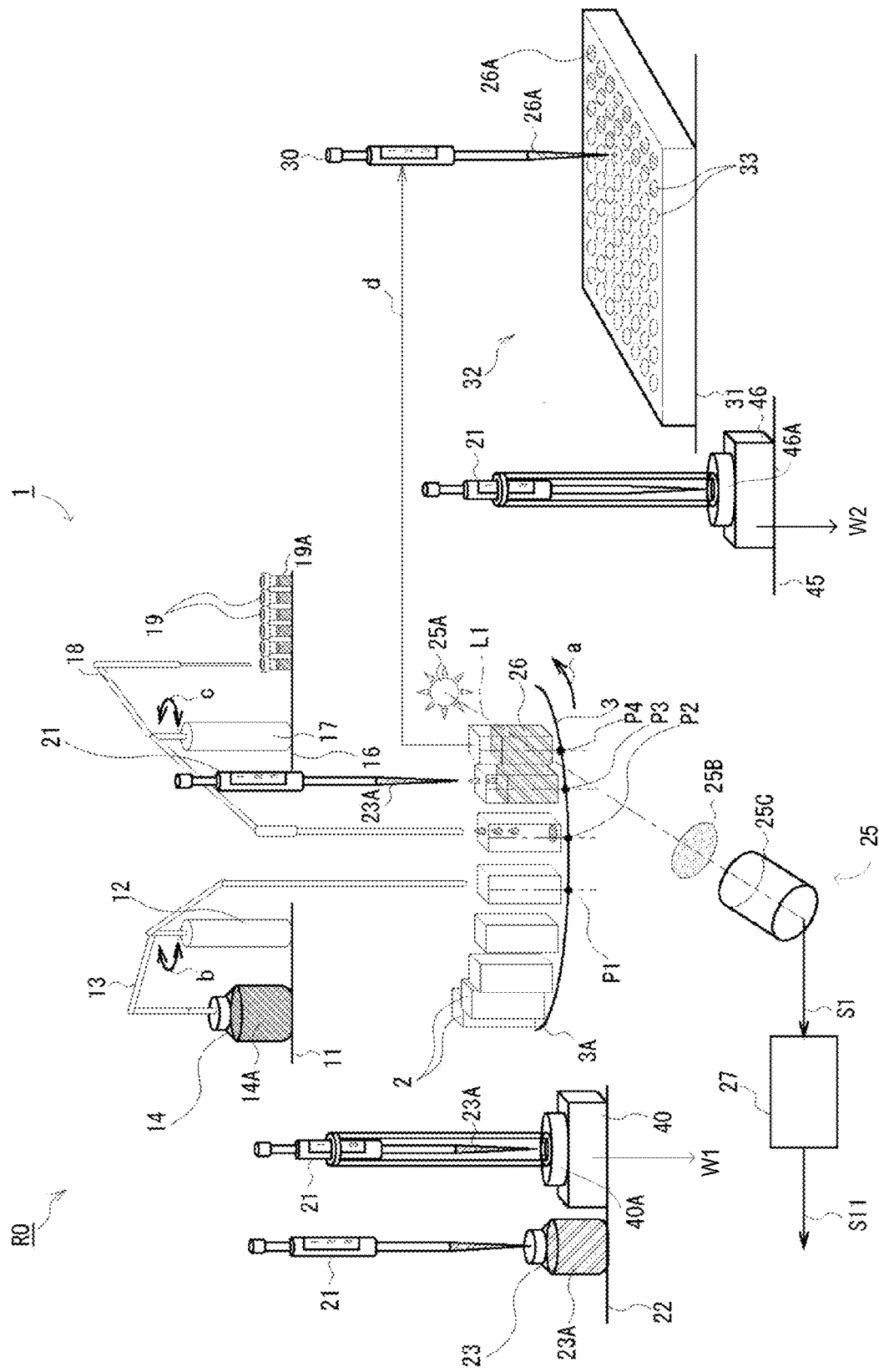
FIG. 1 is a schematic system diagram showing an embodiment of the present method.

A clinical biochemistry automated analyzer R0, which is the validation target of the automated analyzer validation device 1, holds sample blood serving as an analysis target in sample cups 19 on a sample rack 16, dispenses a small prescribed amount of the sample blood from each of the sample cups 19 with a dispensing tube 18 that rotates in the direction indicated by arrow c in a sample filling unit 17 that composes a first analysis target filling unit, and fills the sample blood into optical analysis cells 2.

In addition, the clinical biochemistry automated analyzer R0 holds a sample reagent, which develops a color by reacting with a serum component to be analyzed at normal temperature, in a reagent bottle 14 on a reagent rack 11, dispenses a small prescribed amount of the reagent with a dispensing tube 13 that rotates in the direction indicated by arrow b in a reagent filling unit 12 that composes a second analysis target filling unit, and fills the reagent into the optical analysis cells 2.

A plurality of the optical analysis cells 2 are sequentially arranged along a peripheral edge 3A of a turntable 3 that rotates intermittently in the direction indicated by arrow a, and as a result thereof, when the dispensing tubes 18 and 13 of the sample filling unit 17 and the reagent filling unit 12 have rotated to a prescribed filling position, each of the optical analysis cells 2 is sequentially filled with the sample blood and the coloring reagent.

Thus, the clinical biochemistry automated analyzer R0 serving as the validation target of the automated analyzer validation device 1 is able to automatically analyze sample blood dispensed from the plurality of sample cups 19A based on a chemical component contained in the serum thereof reacting in the optical analysis cells 2.

In FIG. 1, during a typical automated analysis operation, the automatic analyzer validation device 1 fills a dye solution having a first dye (red and blue) serving as the sample liquid 19A into the sample cups 19 serving as liquid retention portions that hold the sample blood when validating the clinical biochemistry automated analyzer R0 serving as the validation target.

As a result, the automated analyzer validation device 1 in the case of FIG. 1 validates the amount dispensed by the sample dispensing unit 17.

In the automated analyzer validation device 1, when the turntable 3 of the clinical biochemistry automated analyzer R0 has been rotated intermittently in the direction indicated by arrow a, the optical analysis cells 2 are sequentially positioned at a reagent filling position P1, a sample filling position P2, a diluent filling position P3 and a target measuring position P4.

When an optical analysis cell 2 has been positioned at the sample filling position P2, the automated analyzer validation device 1 dispenses a prescribed amount of the sample liquid 19A from the plurality of sample cups 19 with the dispensing tube 18 of the sample filling unit 17 provided on the sample rack 16 and fills the sample liquid 19A into the optical analysis cell 2.

Incidentally, the amount dispensed by the sample filling unit 17 at this time is equal to the amount of sample blood dispensed when the clinical biochemistry automated analyzer R0 performs automated analysis.

The sample filling unit 17 aspirates the sample liquid 19A from the plurality of sample cups 19 arranged in a row on the sample rack 16, and as indicated by arrow c, rotates the dispensing tube 18 from the position of the sample cups 19 to the sample filling position P2 and fills the aspirated sample liquid 19A into the optical analysis cells 2 followed by returning the dispensing tube 18 to its original position of the sample cups 19.

In the case of this embodiment, a first dye solution is used for the sample liquid 19A that demonstrates the optical characteristic of absorbing an optical component having a wavelength of 520 nm and 730 nm due to a first red and blue dye.

This first dye solution is a dye solution that contains uncertainty with respect to the red dye solution defined in the previously mentioned international standard ISO8655-7, and is referred to as a "traceable first dye solution" since this characteristic can be made to be traceable to the above-mentioned standard in consideration of this "uncertainty".

The automated analyzer validation device 1 is made to fill a diluent 23A from the diluent dispensing pipetter 21 when the optical analysis cells 2 have been positioned at the diluent filling position P3.

Dispensing work performed by the diluent dispensing pipetter 21 is carried out manually by an analysis technician of the clinical biochemistry automated analyzer R0.

During this dispensing work, a dispensing technician operates the diluent dispensing pipetter 21 and first aspirates a prescribed amount of a diluent 23A from a diluent bottle 23 serving as a liquid holding portion arranged on a diluent rack 22.

In the case of this embodiment, a second dye solution is used for the diluent 23A that demonstrates the optical characteristic of absorbing an optical component having a wavelength of 730 nm due to a second blue dye.

This second dye solution is a dye solution that contains uncertainty with respect to the blue dye solution defined in the previously mentioned international standard ISO8655-7, and is referred to as a "traceable second dye solution" since this characteristic can be made to be traceable to the above-mentioned standard in consideration of this "uncertainty".

When an optical analysis cell 2 has reached the target measuring position P4 as a result of rotation of the turntable 3, the automated analyzer validation device 1 detects the optical absorbance of a measurement target liquid 26 contained in the optical analysis cell 2 with an optical absorbance detection unit 25, and transmits an optical absorbance detection signal S1 to a target measurement result processing unit 27 having the configuration of a microcomputer.

In this embodiment, the optical absorbance detection unit 25 comprises a detecting light L1 emitted from a white light source 25A being passed through the optical analysis cell 2, the optical absorbance detection unit 25 extracts a light component of a prescribed measurement wavelength range with a filter 25B and allows the light to enter a photoelectric converter 25C.

As a result, the detecting light L1 enters the filter 25B after the optical component of a wavelength corresponding to the optical absorbance characteristics of the dye present in a measurement target liquid 26 has been absorbed as a result of passing through the measurement target liquid 26.

In this embodiment, the measurement target liquid 26 contains a 520 nm and 730 nm wavelength components possessed by the red and blue dye solution 19A filled into the optical analysis cells 2 at the sample filling position P2, and a 730 nm wavelength component possessed by the blue dye solution 23A filled at the diluent filling position P3.

Figure 2:
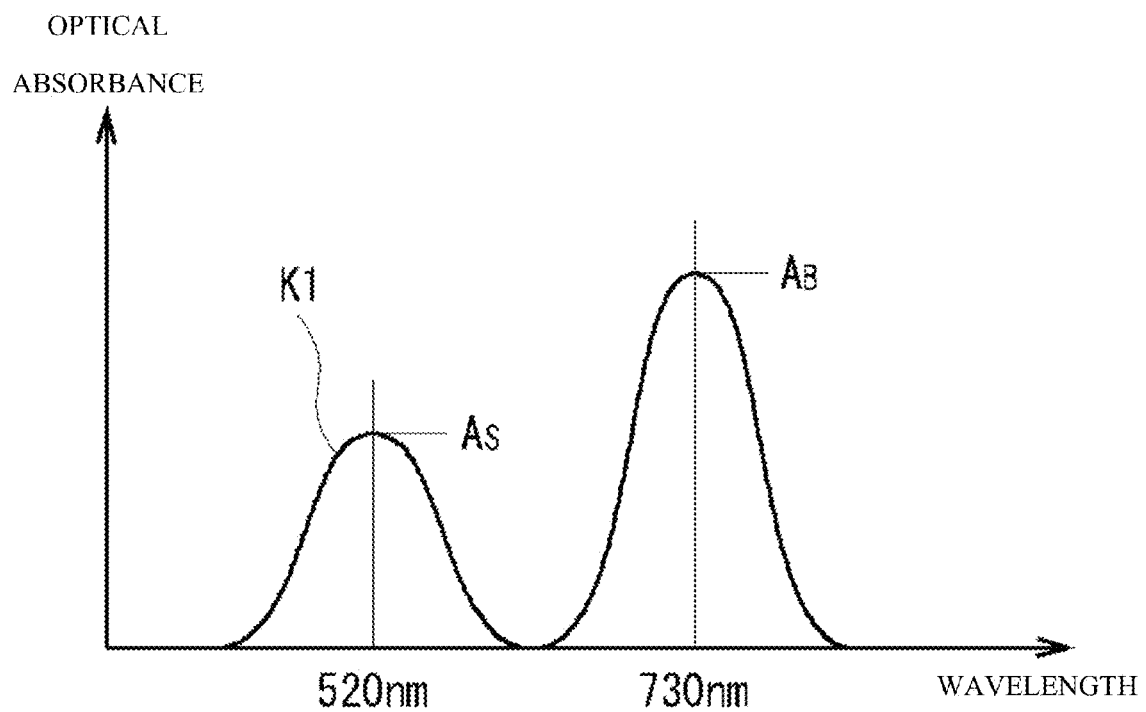
FIG. 2 is a typical absorbance curve results of the present method.

Thus, the wavelength components of the measurement target liquid 26 in the optical analysis cells 2 at the target measuring position P4 are absorbed in accordance with the optical absorbance curve K1 shown in FIG. 2 for the 520 nm and 730 nm wavelength components.

As a result, in the optical absorbance detection unit 25, by calculating the following by the target measurement result processing unit 27 based on the ratio of the optical absorbance of the two wavelength components:

$$V_S = V_B \left[ \frac{\frac{A_S}{A_B}}{K - \frac{A_S}{A_B}} \right] \quad (1)$$

$V_S$=volume of red dye solution
$V_B$=volume of blue dye solution
$A_S$=optical absorbance of red dye solution (520 nm)
$A_B$=optical absorbance of blue dye solution (730 nm)
K=correction value determined at time of shipment from factory the dispensed amount of the sample liquid 19A in the form of the red dye solution can be determined based on the dispensed amount of the diluent 23A and sample liquid 19A in the form of the blue dye solution.

Here, formula (1) is specified as a liquid volume measurement method, based on the dye method according to international standard ISO8655-7, and indicates that the amount of the sample liquid 19A dispensed by the dispensing tube 18, namely the volume $V_S$ of the sample liquid 19A, can be determined as a value obtained by multiplying the ratio of the optical absorbance $A_S$ of the sample liquid 19A in the form of the red dye solution to the optical absorbance $A_B$ (blue dye) of the diluent 23A and sample liquid 19A by the dispensed amount of the diluent in the form of the blue dye solution by the diluent dispensing pipetter 21, namely the volume $V_B$ of the diluent 23A and sample liquid 19A. Formula (1) above is a basic formula to facilitate understanding of the dual dye ratio method. Details regarding calibration of amount dispensed by the dispensing tube will be described by modified formulas or equations as describedbelow herein. These modified formulas theoretically relate to formula (1) above.

In addition, since the ratio of the optical absorbance $A_S$ of the sample liquid 19A in the form of the red dye solution to the optical absorbance $A_B$ of the diluent 23A and sample liquid 19A in the form of the blue dye solution represents the degree of dilution of the sample liquid 19A in the form of the red dye solution relative to the diluent 23A and sample liquid 19A in the form of the blue dye solution, this indicates that the injection volume $V_S$ of the sample liquid 19A can be determined as the ratio of the injection volume of the sample liquid 19A to the volume of the diluent 23A and sample liquid 19A contained in the optical analysis cells 2.

In this manner, the optical absorbance detection unit 25 and the target measurement result processing unit 27 compose a target liquid volume measurement unit for the measurement target liquid 26 in the optical analysis cells 2 at the target measuring position P4.

As indicated by arrow d, the entire volume of the measurement target liquid 26 filled into the optical analysis cells 2 at the target measuring position P4 is removed as a measurement target transfer liquid 26A by a dispensing technician using the transfer pipetter 30, and transferred to a reference value measurement microplate 32 on a reference value rack 31.

The entire volume of the measurement target liquid 26 is aspirated from the optical analysis cells 2 with the transfer pipetter 30 during manual work performed by a dispensing technician in the same manner as previously described with respect to the diluent dispensing pipetter 21, and the measurement target liquid 26 is transferred to one of a plurality of retention wells 33 provided in the reference value measurement microplate 32.

In addition to having the configuration previously described, the validation device 1 is provided with a balance 40A that composes the diluent weighing unit 40 on the diluent rack 22.

The balance 40A of the diluent weighing unit 40 weighs the total weight of the diluent dispensing pipetter 21 and the diluent 23A contained therein as a result of a dispensing technician dispensing the diluent 23A from the diluent bottle 23 using the diluent dispensing pipetter 21, and placing on the balance 40A that composes the diluent weighing unit 40.

In addition to recording the result W1 of weighing in the diluent weighing unit 40, the dispensing technician fills the diluent 23A by transporting the diluent dispensing pipetter 21 retaining the dispensing liquid 23A to the optical analysis cells 2 at the diluent filling position P3.

Following this dispensing work, an operator executing diluent operation places the diluent dispensing pipetter 21 that has currently been used on a balance 46A that composes the pipetter weighing unit 46 provided on a pipetter rack 45 for a weight result W2. It is within the scope of the present method to use weighing unit 46 to obtain this weight measurement for the empty pipette 21.

At this time, the pipetter weighing unit 46 determines the weight of the diluent dispensing pipetter 21 after having emptied the diluent 23A into optical analysis cell 2, and the dispensing technician records the result of that weighing.

In this manner, the weight of the diluent 23A filled into the optical analysis cells 2 by the dispensing technician at the diluent filling position P3, and thus the amount of the diluent 23A dispensed by the diluent dispensing pipetter 21, can be determined by a gravimetric method by comparing the weighing result obtained from the diluent weighing unit 40 and the weighing result obtained from the pipetter weighing unit 46.

Figure 3:
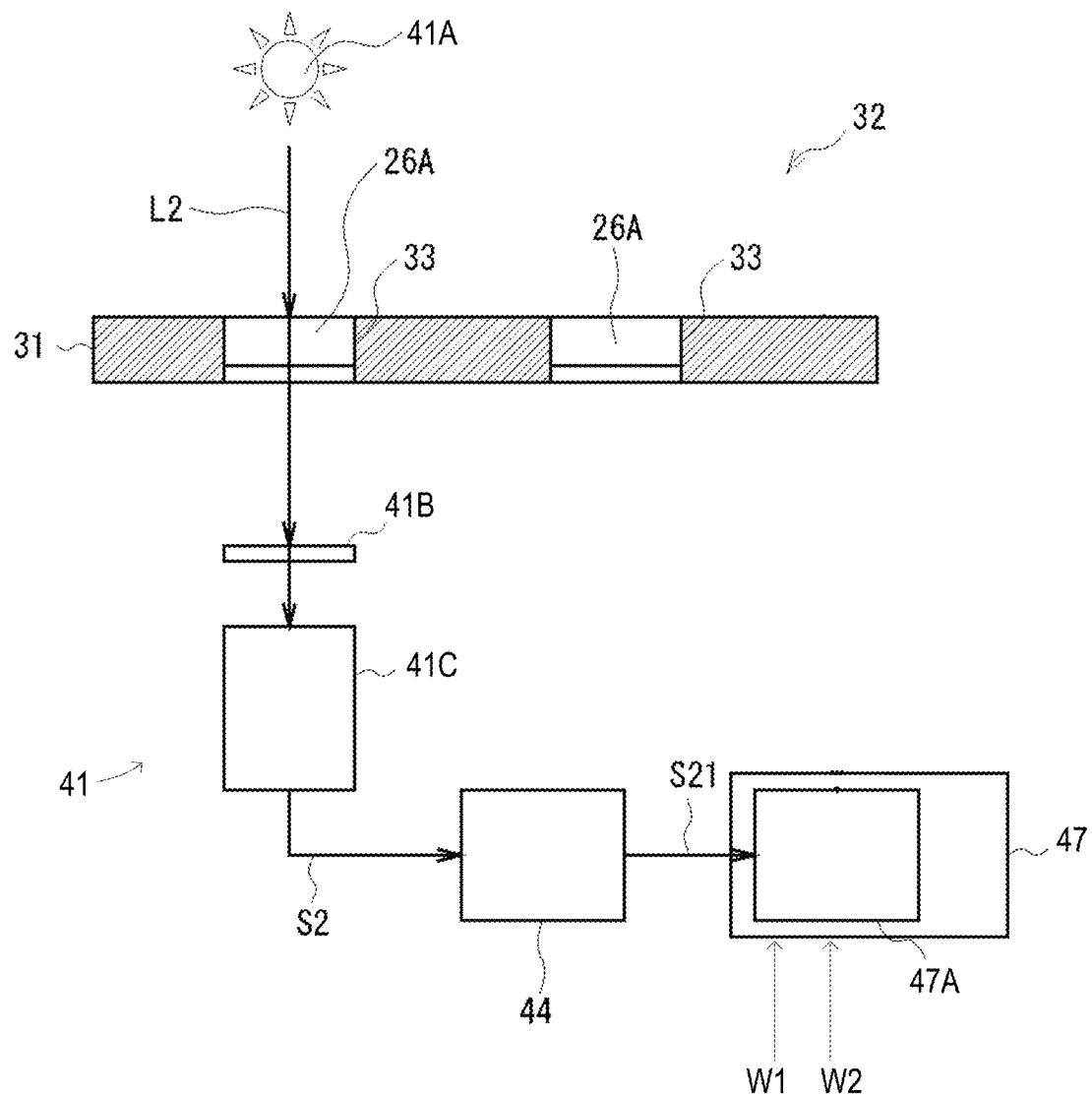
FIG. 3 is a schematic system diagram showing the configuration of the second optical absorbance detection unit and a reference value measurement microplate.

As shown in FIG. 3, a second optical absorbance detection unit 41 is used to measure the amount of the measurement target transfer liquid 26A placed in the retention wells 33 of the reference value measurement microplate 32 using a dye method as a highly accurate reference value. The total volume of the measurement target transfer liquid 26A will be calculated by the equations presented as described below herein.

The optical absorbance detection unit 41 has a white light source 41A that emits a white light L2, and causes the white light L2 to enter a photoelectric converter 41C with respect to a filter 41B after having passed through the measurement target transfer liquid 26A.

Here, as was previously described with respect to FIG. 2, the measurement target transfer liquid 26A has optical absorbance characteristics such that a blue dye component of a wavelength of 730 nm of the diluent 23 and sample liquid 19A and a red dye component of a wavelength of 520 nm of the sample liquid 19A are absorbed as represented by the optical absorbance curve K1, and the filter 41B extracts light of a wavelength range that includes these dye components followed by the light entering the photoelectric converter 41C.

The photoelectric converter 41C is configured so as to arithmetically process the above-mentioned formula (1) at high accuracy, including uncertainty (thus, making it traceable), based on the specifications of the previously described international standard ISO8655-7, and as a result, an optical absorbance detection signal S2 obtained from the photoelectric converter 41C is transmitted to a reference measurement result processing unit 44 having the configuration of a microcomputer as a reference value representing the volume of the sample liquid 19A contained in the measurement target transfer liquid 26A at a high level of accuracy that is close to that of the measurement result obtained with a standard equivalent to the device of the aforementioned international standard.

In this manner, the reference measurement result processing unit 44 retains the measurement result of the volume of the sample liquid 19A contained in the measurement target transfer liquid 26A with high accuracy as a reference value.

The optical absorbance detection unit 41 determines measured values for reference values in this manner for the measurement target transfer liquid 26A retained in all of the retention wells 33 of the reference value measurement microplate 32, and accumulates those measured values in the reference measurement result processing unit 44.

The reference value measurement result accumulated in the reference measurement result processing unit 44 of the reference value judgment unit 32 is transmitted to the dispensing accuracy judgment unit 47A of the validation result processing unit 47 as a reference liquid volume signal S21.

The dispensing accuracy judgment unit 47A determines the reference liquid volume signal S21 obtained from the reference value measurement result processing unit 44, and validation result processing unit 47 confirms the amount dispensed by the diluent dispensing pipetter 21 using a gravimetric method based on the weighing results W1 and W2 of the diluent weighing unit 40 and the pipetter weighing unit 46, respectively, as a validation result that expresses the measuring limit (uncertainty) of the clinical biochemistry automated analyzer R0 serving as the validation target.

It is within the scope of the present method to have the target measurement result processing unit 27, the reference value measurement result processing unit 44 and the validation result processing unit 47 be a single microprocessor or computer or be distributed as shown.

Figure 4:
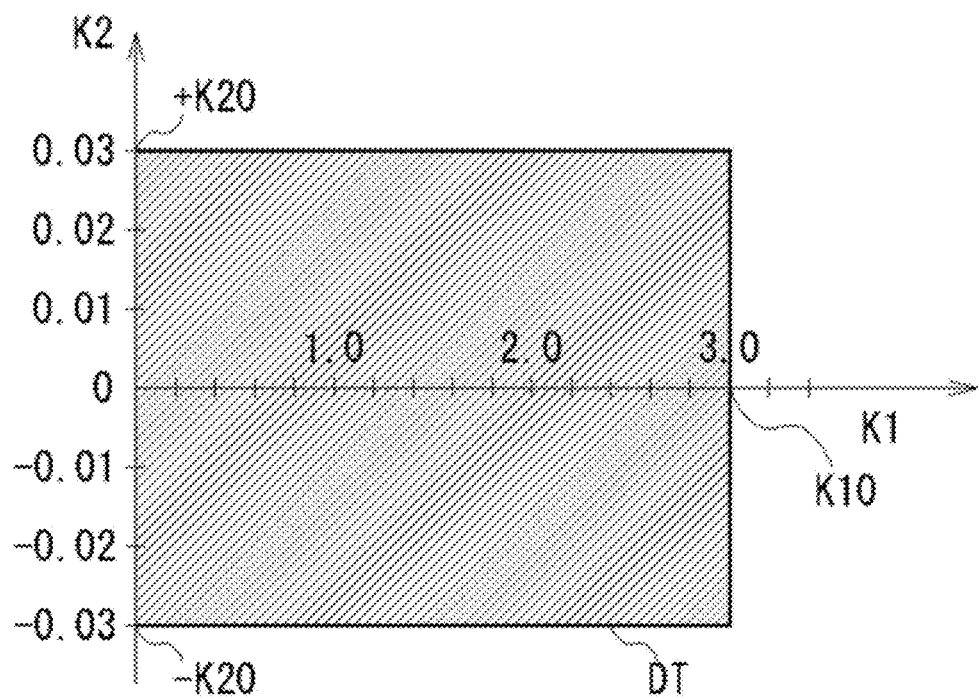
FIG. 4 is a typical graphical representation of the validation/calibration results of the present method.

As shown in FIG. 4, in addition to plotting a coefficient of variation K1 within the range of 0% to 3.0% on the horizontal axis, by further plotting a degree of accuracy K2 within the range of −0.03 to +0.03 on the vertical axis, this validation result can be expressed according to whether or not the dispensing accuracy for the amount of the sample liquid 19A dispensed from the sample cups 19 by the sample filling unit 17 lies within a dispensing accuracy curve DT.

Here, the coefficient of variation K1 represents the degree of variation of the validation result, while the degree of accuracy K2 is equal to 0 when the validated dispensing amount is the true value, and the degree of variation from the true value K2=0 is represented as K2+0.01, +0.02 . . . or −0.01, −0.02 . . . .

In this manner, when a validation result is within an area demarcated by the dispensing accuracy curve DT that passes through a target coefficient of variation K1=0 to K=10 and a target degree of accuracy K2=+K20 to −K20, the dispensing accuracy of the automated analyzer serving as the validation target is validated to be within the allowed range.

The method provides an automated analyzer R0 is the validation target that sequentially carries out automated analyses by dispensing an automated analysis target liquid 19A into a plurality of optical analysis cells 2 by way of sample filling unit 17. A first dye solution 19A is sequentially filled into the plurality of optical analysis cells 2 dispensing from a first liquid holding unit 19, and together with dispensing a second dye solution 23A from a second liquid holding unit 23 through the use of a diluent dispensing pipetter 21. The total weight of the diluent dispensing pipetter 21 in the dispensing state, i.e., with the dye solution, is obtained, based on a gravimetric method, using a diluent weighing unit 40. The second dye solution 23A is dispensed into the optical analysis cells 2 which is already filled with the first dye solution 19A.

Thereafter, determining the amounts of liquid in the optical analysis cells 2 filled with the first and second dye solutions 19A and 23A by using an optical absorbance detection unit 25 to determine a light path length of optical analysis cells 2 with the equation presented as described beow herein, weighing the emptied diluent dispensing pipetter 21 (after having been filled with the second dye solution 23A) using a pipetter weighing unit 46, based on a gravimetric method. Transferring the contents of the optical analysis cells 2 filled with the first and second dye solutions 19A and 23A to a reference value measurement microplate 32 using a transfer pipetter 30 and measuring (based on a dual dye ratio method) using a second optical absorbance detection unit 41 to obtain a reference measured value. Performing a computational analysis using all of the measured results obtained by the present method to validate the dispensing accuracy of the sample filling unit 17 of the automated analyzer R0 by determining any deviation between and among the reference measured value and the target measured value determined based on a dye method and the deviation between measurement results of the pipetter weighing unit 46 and the diluent weighing unit 40 determined based on a gravimetric method.

Figure 5:
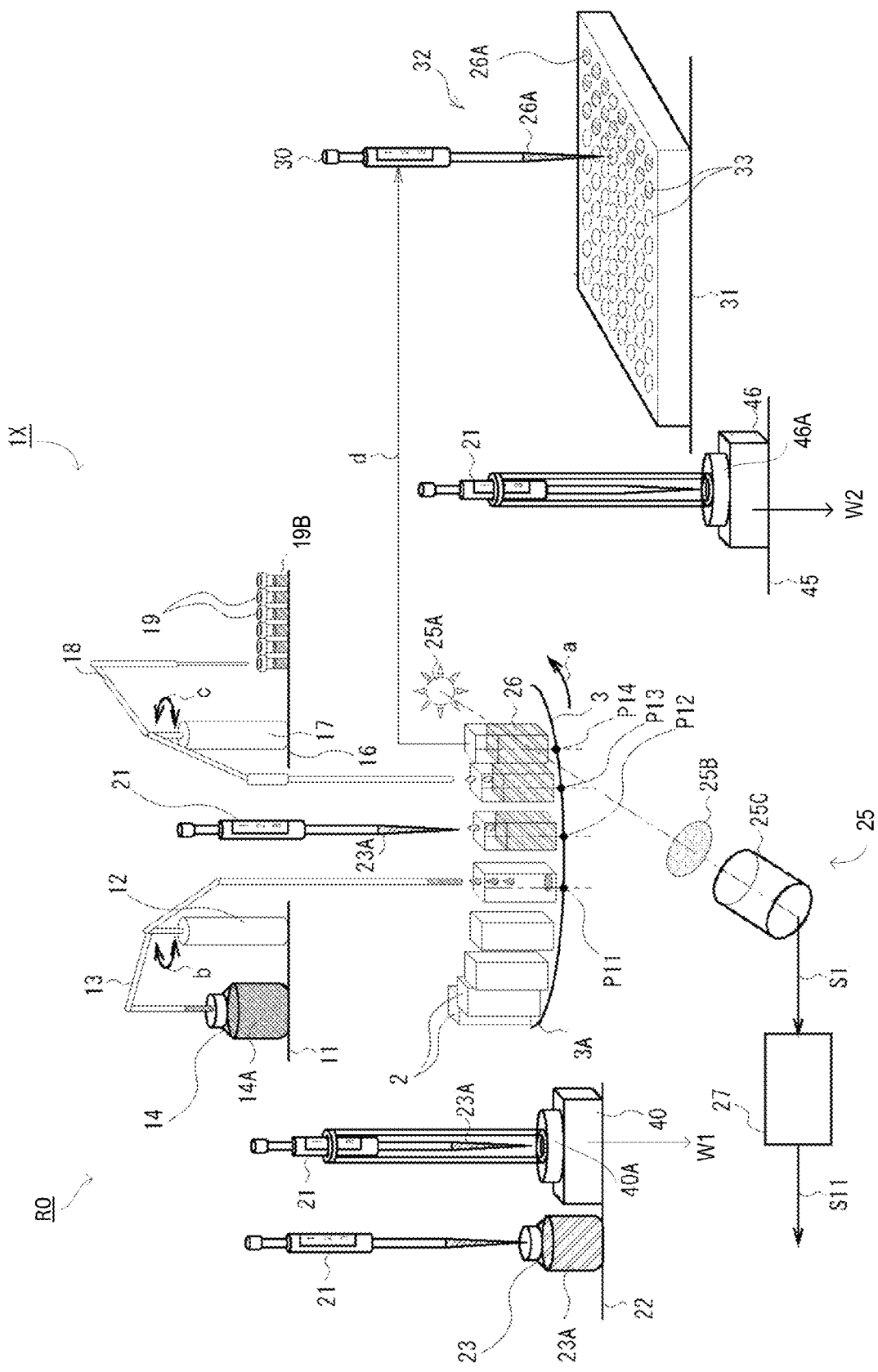
FIG. 5 is a schematic system diagram showing a second embodiment of the present method.

In FIG. 5, another embodiment of the present method, the same reference symbols are used to indicate those elements and features corresponding to FIG. 1.

The automated analyzer validation device 1X of FIG. 5 differs from the automated analyzer validation device 1 of FIG. 1 in that, in contrast to the automated analyzer validation device 1 of FIG. 1 (directed to determining the dispensed amount of the sample liquid 19A that is a red dye solution based on the dispensed amount of the diluent 23A that is blue dye solution using a dye method), the validation device 1X of FIG. 5 determines the dispensed amount of a reagent solution 14A that is a red and blue dye solution based on the dispensed amount of the diluent 23A and the sample liquid 19B that are blue dye solutions.

Namely, in the case of FIG. 5, the reagent solution 14A dispensed from the reagent bottle 14 is filled into optical analysis cells 2 on the turntable 3 by a reagent filling unit 12 at a reagent filling position P11.

In this case, a first dye solution demonstrating the optical characteristic of absorbing an optical component having a wavelength of 520 nm and 730 nm due to the first red and blue dye is used for the reagent solution 14A.

Continuing, the diluent 23A manually dispensed from the diluent bottle 23 by a dispensing technician is filled into the optical analysis cells 2 by the diluent dispensing pipetter 21 at a diluent filling position P12.

In this case, a second dye solution demonstrating the optical characteristic of absorbing an optical component having a wavelength of 730 nm due to the second blue dye is used for the diluent 23A.

Here, prior to filling the diluent 23A at the diluent filling position P12, the diluent dispensing pipetter 21 in the state of having dispensed the diluent 23A is placed on the balance 40A that composes the diluent weighing unit 40 and the total weight thereof is weighed.

After having filled the diluent 23A, the diluent dispensing pipetter 21 is placed on the balance 46A that composes the pipetter weighing unit 46 and the weight of the pipetter 21 is weighed.

Continuing, the sample liquid 19B dispensed from the sample cups 19 by the sample filling unit 17 is filled into the optical analysis cells 2 at a sample filling position P13.

In this case, a third dye solution demonstrating the optical characteristic of absorbing optical components having a wavelength of 730 nm due to the second blue dye in the same manner as the above-mentioned diluent 23A is used for the sample liquid 19B.

Continuing, the optical absorbance of the measurement target liquid 26 in the optical analysis cells 2 is detected by the optical absorbance detection unit 25 at a measurement target position P14.

Accompanying this, the entire volume of liquid filled into the optical analysis cells 2 is transferred to a reference value measurement microplate 32 by the transfer pipetter 30 at the target measuring position P14 as indicated by arrow d.

In the configuration of FIG. 5, when an optical analysis cell 2 has been brought to the reagent filling position P11 by the turntable 3, the validation device 1X dispenses a first dye solution in the form of the reagent solution 14A from the reagent bottle 14 with the dispensing tube 13 of the reagent filling unit 12 and fills the optical analysis cell 2.

Continuing, after the second dye solution in the form of the diluent dispensed by the diluent dispensing pipetter 21 from the diluent bottle 23 by a dispensing technician has been filled into the optical analysis cells 2 filled with the reagent solution 23A at the diluent filling position P12, the detection device 1X fills the third dye solution in the form of the sample liquid dispensed from the sample cups 19 by the sample filling unit 17 into the optical analysis cells 2 at the sample filling position P13.

In this manner, as a result of the first dye solution of the first red and blue dye filled at the reagent filling position P11, the second dye solution of the second blue dye filled from the diluent dispensing pipetter 21 at the diluent filling position P12, and the third dye solution of the second blue dye filled by the sample filling unit 17 at the sample filling position P13 being mixed in the optical analysis cells 2, the optical absorbance detection unit 25 detects optical absorbance at the measurement target position P14 by using this mixture as the measurement target liquid 26.

At this time, the optical absorbance detection unit 25 determines the volume of the red and blue reagent solution 14A serving as the first dye based on the ratio between the optical absorbance of the reagent solution 14A serving as the red wavelength component of the first dye and the optical absorbance of the diluent solution 23A and the sample liquid 19B serving as blue wavelength components of the second dye in accordance with the above-mentioned formula (1)

using a dye method based on the specifications of ISO8655-7, and accumulates that volume in the target measurement result processing unit 27.

Here, in conjunction with the liquid volume of the second dye (blue), although error occurs in the liquid volume of the first dye (red and blue) in the above-mentioned formula (1) due to the sample liquid 19B having been filled into the diluent 23A, if the amount of the diluent 23A (namely, the second dye solution) that composes the liquid volume of the second dye (blue) is known and the amount of the sample liquid 19B (namely, the third dye solution) is known, then the amount of the reagent solution 14A of the first dye (namely, the first dye solution) can be determined with high accuracy with almost no effect of evaporation in the dye method.

When this is done, in the case of FIG. 5 as well, in addition to weighing the total weight, including the diluent 23A dispensed from the diluent bottle 23 by the diluent dispensing pipetter 21 in the diluent weighing unit 40, a dispensing technician also weighs the weight of the diluent dispensing pipetter 21 after having filled the diluent 23A at the diluent filling position P12 in the pipetter weighing unit 46.

In this manner, the amount of the diluent 23A dispensed by the diluent dispensing pipetter 21 can be confirmed by a gravimetric method according to the difference between the weighing result of the diluent weighing unit 40 and the weighing result of the pipetter weighing unit 46.

In addition, the dispensed amount of the measurement target transfer liquid 26A transferred to the retaining wells 33 of the reference value measurement microplate 32 by the transfer pipetter 30 is determined as a highly accurate reference value corresponding to a standard based on the dye method by the reference value measurement microplate 32 of FIG. 3.

This reference value judgment result represents the dispensed amount of the red component contained in the measurement target transfer liquid 26A transferred by the transfer pipetter 30, namely the dispensed amount of the reagent solution 14A of the first dye solution dispensed from the reagent bottle 14 by the reagent filling unit 12, and this is accumulated in the reference value judgment result processing unit 44 of the reference value measurement microplate 32.

In this manner, the validation result processing unit 47 of the reference value measurement microplate 32 is able to determine a dispensing accuracy curve DT as previously described with respect to FIG. 4 and the reference liquid volume signal S21 obtained from the reference value measurement result processing unit 44.

As a result, the validation device 1X of FIG. 5 is able to validate the dispensing accuracy of the reagent filling unit 12 of the clinical biochemistry automated analyzer R0 serving as the validation target based on the resulting dispensing accuracy curve DT.

In this manner, the liquid volume of the blue dye component can be measured according to the equations presented as described below herein and this can be confirmed as the liquid volume $V_B$ of the blue dye liquid in the arithmetic processing of the aforementioned formula (1) based on a dye method, thereby making it possible to even more reliably confirm certainty with respect to results of measuring the dispensed amount of the red component.

Incidentally, if the amount of the reagent solution 14A dispensed by the reagent filling unit 12 is determined according to a dye method using the configuration shown in FIG. 5 after having determined the amount of the sample liquid 19B dispensed by the sample filling unit 17 according to a dye method using the validation device 1 having the configuration shown in FIG. 1, validation of the dispensed amount of the sample filling unit 17 used to dispense blood and validation of the dispensed amount of the reagent filling unit 12 used to dispense a coloring reagent, which are both important elements of analysis results in the clinical biochemistry automated analyzer R0, can be carried out with high accuracy.

The method of FIG. 5 provides an automated analyzer R0 is the validation target that sequentially carries out automated analyses by respectively dispensing an automated analysis target liquid 14A into a plurality of optical analysis cells 2 by first and second analysis target liquid filling units 12 and 17. A first dye solution 14A is sequentially filled into the plurality of optical analysis cells 2 by dispensing from a first liquid holding unit 14 by using the first analysis target liquid filling unit 12, and together with dispensing a second dye solution 23A from a second liquid holding unit 23 using a diluent dispensing pipetter 21, the total weight of the diluent dispensing pipetter 21 with the second dye solution 23A is weighed by a diluent weighting unit 40, based on a gravimetric method. A third dye solution 19B, which the same dye as the second dye solution 23A, is dispensed into the optical analysis cells 2 filled with the first and second dye solutions 14A and 23A from a sample cup 19 by using the sample filling unit 17.

Measuring the amounts of liquid in the optical analysis cells 2 filled with the first, second and third dye solutions, i.e., 14A, 23A and 19B, respectively, by an optical absorbance detection unit 25 in order to determine the light path length of optical analysis cells 2 as a target value measurement result. Obtaining the weight of the diluent dispensing pipetter 21 after having been filled with the second dye solution 23A by a pipetter weighing unit 46 based on a gravimetric method.

Transferring the entire content from the optical analysis cells 2 filled with the first, second and third dye solutions, i.e., 14A, 23A and 19B, respectively, to a reference value measurement microplate 32 by using a transfer pipetter 30. Based on a dual dye ratio method, using a second optical absorbance detection unit to determine the amount of the first dye solution 14A as a reference value measurement result. Performing a computational analysis to validate the dispensing accuracy of the analysis target liquid filling unit 12 of the automated analyzer R0, according to any deviation between and among the reference value measurement result and the target value measurement result, determined based on a dual dye ratio method, and the measurement results of the pipetter weighing unit 46 and the diluent weighing unit 40 determined to prove that almost no residual amount of transfer volume based on a gravimetric method.

Although the above-mentioned embodiments described in the present disclosure refer to a clinical biochemistry automated analyzer used for haematological testing, the present disclosure is not limited thereto, but rather can also be applied to a wide range of other clinical biochemistry automated analyzers.

It is also within the scope of the present disclosure to have the manual pipetting of the dye solutions and target liquids performed by a robotic handling device or automated dispensing units to have a fully automated process. In addition, the weighing of the pipette may be performed on a single weighing unit.

Figure 6:
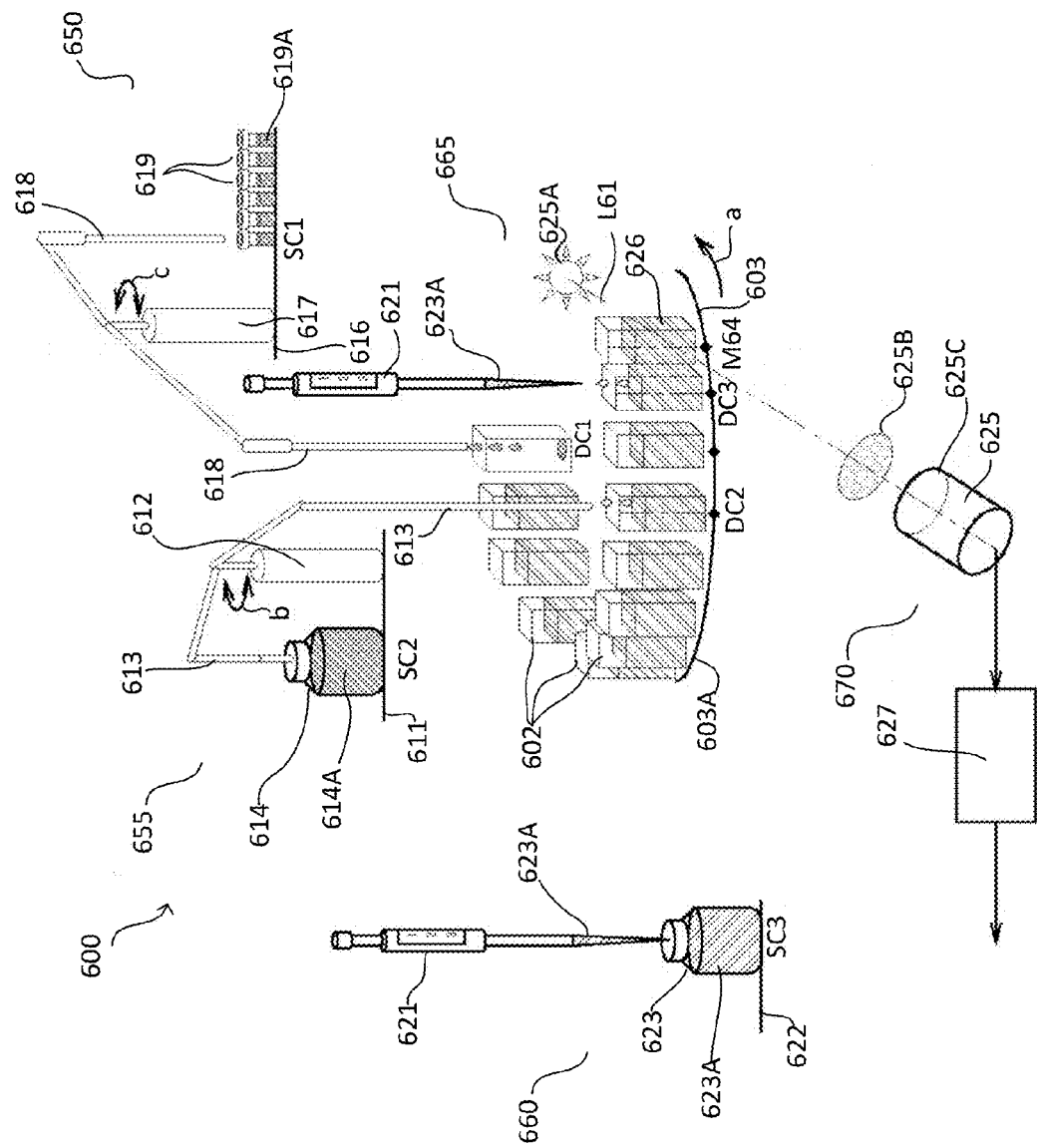
FIG. 6 shows a simplified diagram of an automated analyzer.

FIG. 6 shows a simplified diagram of an automated analyzer 600. The automated analyzer 600 is similar to the automated analyzer R0 as described in FIG. 1. As such, common features or elements may not be described or described in detail.

The automated analyzer 600, for example, includes a sample section 650, a reagent section 655, a dilution section 660, a reaction section 665 and an analysis section 670. The automated analyzer may also include other suitable sections.

The sample section 650 has a sample rack or sample table 616 and a drive unit (not shown) for rotating the sample table. The sample table includes a plurality of holes on the periphery thereof to hold a plurality of sample cups 619. The sample cups are filled with sample solution 619A. The sample solution includes one or more components to be analysed. These sample cups are to be transferred to a suction position SC1 by rotation of the sample table as required. The sample section includes a rotatable sample dispensing unit 617 having an arm for holding an automated sample dispensing tube or pipette 618. The sample dispensing unit includes a drive unit which enables the sample dispensing pipette to move and rotate between the suction position to a discharge position DC1 in a direction indicated by arrow c.

The reagent section 655 includes similar configuration as the sample section. As shown, the reagent section has a reagent rack or reagent table 611 and a drive unit (not shown) for rotating the reagent table. The reagent table holds a reagent bottle 614. Although one reagent bottle is shown, it is understood that there could be more than one reagent bottle. The reagent bottle is filled with a reagent solution 614A which develops a color by reacting with a component of the sample solution to be analysed. The reagent bottle is to be transferred to a suction position SC2 by rotation of the reagent table as required. The reagent section also includes a rotatable reagent dispensing unit 612 having an arm for holding an automated reagent dispensing tube or pipette 613. The reagent dispensing unit includes a drive unit which enables the reagent dispensing tube to move and rotate between the suction position to a discharge position DC2 in a direction indicated by arrow b.

The reaction section 665 includes a reaction turntable 603 and a drive unit (not shown) for rotating the reaction turntable. The reaction turntable has a plurality of holes for holding a plurality of optical analysis cells 602. The optical analysis cells, for example, are of rectangular shape and are transparent. The optical analysis cells, for example, may be made of moulded plastics or glass. The optical analysis cell may be made of other suitable materials or in other suitable shapes as long as it allows for optical or photometric measurement to be performed. The plurality of optical analysis cells are sequentially arranged along a peripheral edge 603A of the turntable that rotates intermittently in a counter clockwise direction indicated by arrow a. It is understood that the turntable may also rotate in a clockwise direction. The reaction section also includes a light source 625A.

The diluent section 660 includes a diluent rack or table 622. The diluent table holds a diluent bottle 623. Although one diluent bottle is shown, it is understood that there could be more than one diluent bottle. The diluent bottle is filled with a diluent solution 623A which dilutes the sample solution. The diluent section includes a diluent dispensing pipette 621. The diluent dispensing pipette may be moved between a suction position SC3 at the diluent table and a discharge position DC3 at the reaction turntable. Although the diluent dispensing pipette is shown as a manual dispensing pipette, it is understood that the diluent section may include an automated diluent dispensing unit having a rotatable arm which holds the diluent dispensing pipette.

The analysis section 670 includes an optical absorbance detection unit 625. The optical absorbance detection unit, for example, is a photometer. The analysis section includes a filter 625B which allows the photometer to extract a light component of a prescribed measurement wavelength range. The analysis section also includes a photoelectric converter 625C for converting a measurement signal according to the intensity of the transmitted light into a digital signal. The analysis section includes a processing unit 627 having at least a microcomputer and a display unit. The microcomputer controls the operation of the sample, reagent and reaction sections. The display unit displays the conditions of analysis, such as dispensing volumes of the sample solution, reagent solution and dilution solution as well as the absorption measurement results obtained from the photometer for analysis of the component of the sample solution.

The automated analyzer 600 may be used to perform clinical analysis of particular components of a sample quickly and with minimal operator requirement. For example, the automated analyzer may be used to assess or calculate the amount of a particular component within a sample. For instance, during normal operation of the automated analyzer, the sample cups of the sample section are used to hold sample solution 619A, such as blood or serum. In such case, the automated analyzer, for example, may be used to analyze or calculate the amount of a component within the blood or serum samples, such as albumin, sugar, enzyme, etc. For simplicity and for illustration purpose, serum will be used as an example of the sample solution while albumin will used as an example for the component for analysis for describing the normal operation of the automated analyzer. It is understood that other components of blood or serum may serve as the component for analysis.

A normal operation of the automated analyzer 600 will now be described. A user defines a small prescribed amount of serum and a small prescribed amount of reagent through an input device which is coupled to the microcomputer. The start button of the analyzer is depressed to initiate the analysis process. When a sample cup 619A containing the serum reaches a suction position SC1 by rotation of the sample table 616, the sample dispensing pipette 618 sucks and holds the small prescribed amount of the serum at the suction position on the sample table. The sample dispensing unit then rotates the filled sample dispensing pipette in the direction indicated by arrow c from the suction position to a discharge position. For example, when the sample dispensing pipette reaches the discharge position DC1, such as the specimen input position, it discharges the prescribed amount of serum defined by the user into an empty optical analysis cell 602 at the discharge position on the turntable 603.

The process may continue by rotating the optical analysis cell which is filled with serum to a reagent discharge position. For example, when the optical analysis cell which is filled with serum reaches the reagent discharge position, the reagent dispensing pipette 613 sucks and holds the small prescribed amount of reagent defined by the user at the suction position SC2 on the reagent table 611. The reagent, for example, may be any suitable chemical substance which develops a color by reacting with albumin of the serum. For example, the reagent solution may be bromocresol-green dye which develops a blue-green color when reacting with albumin. The reagent dispensing unit then rotates the filled reagent dispensing pipette in the direction indicated by arrow b from the suction position to the discharge position DC2. For example, when the reagent dispensing pipette reaches the reagent discharge position, it discharges the prescribed amount of bromocresol-green dye into the optical analysis cell which is filled with serum at the discharge position, such as DC2, on the turntable 603.

As described, the analysis process started with the dispensing of the sample solution into an empty optical analysis cell followed by the dispensing of the reagent solution. Alternatively, the analysis process may initiate with dispensing of the reagent solution into an empty optical analysis cell, followed by dispensing of the sample solution into the optical analysis cell filled with reagent. In such case, when the reagent dispensing pipette reaches a reagent discharge position, it discharges the reagent into an empty optical analysis cell. The optical analysis cell which is filled with reagent is rotated to the sample discharge position. The prescribed amount of sample solution is then discharged into the optical analysis cell filled with reagent.

The process continues to rotate the filled optical analysis cell to a diluent discharge position. For example, when the filled optical analysis cell reaches the diluent discharge position DC3, such as the diluent filling position, a prescribed amount of a diluent, such as saline, is dispensed into the optical analysis cell which is filled with serum and bromocresol-green dye. For example, the user manually aspirates a prescribed amount of saline from a diluent bottle 623 using a diluent dispensing pipette 621 and transfers the saline to the filled optical analysis cell at the diluent discharge position. Once the diluent is discharged into the filled optical analysis cell, the sample solution, reagent and diluent are mixed by a mixing mechanism (not shown), such as an agitator, to form a measurement target liquid 626.

The optical analysis cell filled with the measurement target liquid 626 is rotated to a measuring position M64, such as the target measuring position. The measurement target liquid traverses the light from the light source 625A so that the colored condition of the measurement target liquid is observed. Thus, an optical characteristic of the measurement target liquid can be measured several times.

The light L61 from the light source 625A passes through the optical analysis cell which is filled with the measurement target liquid in a horizontal direction. The transmitted light traverses a filter 625B which allows the photometer to extract a light component of a prescribed measurement wavelength range. The filter 625B, for example, may be a 630 nm filter. Other suitable filter may also be used, depending on the dye component of the reagent solution. A signal having a magnitude representative of a transmitted light intensity is supplied to the converter 625C. The analog signal is then converted to a digital signal by the converter and the digital signal is fed to the microcomputer through the interface where necessary operations are carried out and the operation results are stored in a memory. After several times of optical or photometric measurements for the measurement target liquid have been completed, the data obtained in the several times of measurements are compared and processed as required, and a concentration value of the component of analysis is calculated. The analysis process which calculates the concentration value of the component of analysis is displayed at the display unit.

The analysis process performed by an automated analyzer, for example, is to calculate the concentration value of the albumin contained in the serum. As described, during normal operation of the automated analyzer, the bromocresol-green dye reacts with albumin and develops a color, such as blue-green color. Therefore, the concentration of albumin within the serum is the same as the concentration of the bromocresol-green dye or color component of the reagent solution which binds with albumin.

The concentration of the dye component in the optical analysis cell, such as the concentration of the bromocresol-green dye which binds the albumin, is determined via photometric method based on the Beer-Lambert law. This law states that when light passes through a solution containing some concentration of dye or color component, there is a linear relationship between the concentration of the dye component and the amount of energy it absorbs. The Beer-Lambert equation is presented as follows:

$$A_\lambda = \epsilon_\lambda LC \qquad (2)$$

where
- $A_\lambda$ = absorbance of the dye component at a specific wavelength $\lambda$,
- $\epsilon_{80}$ = molar absorptivity, which is a measure of the amount of light absorbed per unit concentration,
- L = path length of the light that passes through the optical analysis cell in which the solution containing some concentration of dye or color component is contained, and
- C = concentration of the dye component in the optical analysis cell.

As shown, equation (2) above illustrates that absorbance ($A_\lambda$) is directly proportional to the other parameters. Thus, this proportionality is used in an automated analyzer to determine the unknown concentration of the dye component in a solution with the condition that the molar absorptivity of particular dye component at the measurement wavelength and the path length of the light through the solution are known or fixed.

Equation (2) above can be rearranged to calculate, for example, the concentration value of the albumin within the serum. When light L61 passes through the colored measurement target solution 626, the intensity of the transmitted light decreases exponentially with the increase in concentration of the absorbing bromocresol-green dye. The amount of the light energy absorbed depends on the number of bromocresol-green dye molecules which react with albumin and the thickness of the measurement target liquid, which is the path length of the light. As such, intensity of light energy leaving the measurement target solution is used to provide the absorbance value of the dye component at 630 nm. Since the absorbance value is obtained from measurement of the intensity of the transmitted light while the molar absorptivity of the dye and the light path length are constant and known, the concentration of the dye which is equivalent to the concentration of albumin can be obtained.

The analysis process to calculate the amount of albumin within the serum in the optical analysis cell is completed. The analysis process may continue with calculation of albumin in subsequent or adjacent optical analysis cell in the automated analyzer.

In the example given above, serum serves as the sample solution, albumin serves as the component of analysis, bromocresol-green dye serves as the reagent solution while saline serves as the diluent. It is understood that other suitable sample solution, component analysis, reagent and diluent solutions may also be useful.

The concentration value of the component of analysis within a sample solution as calculated above is based on the assumption that the various elements of the automated analyzer are operated at precise and accurate conditions. However, I have discovered that this is not always the case and thus the calculated value of the component of analysis in a sample solution by the automated analyzer may not be reliable. For example, I have found that the path length of each optical analysis cells may deviate from the path length dimension provided by the manufacturer of the optical analysis cell. Further, the path length of the optical analysis cell may not be fixed or constant as these optical analysis cells may be replaced with new optical analysis cells after numerous times of usage or certain time period. In addition, wash solution or system solution may be introduced to wash the dispensing pipette after a dispensing operation is performed. However, there may be some residual wash solution which remains in the dispensing pipette. The residual wash solution remaining in the dispensing pipette may cause the actual dispensed volume of the sample dispensing pipette or the reagent dispensing pipette to be below the volume as prescribed or defined by the user. Therefore, to determine whether the automated analyzer is operating in precise and accurate conditions such that the results obtained from the automated analyzer is reliable, it is necessary to verify or validate the accuracy of the light path length of the optical analysis cell and the accuracy of the dispensing volume of the dispensing pipettes of the automated analyzer. Validation of the results obtained from automated analyzer is also necessary to fulfil national or regional compliance.

Figure 7A:
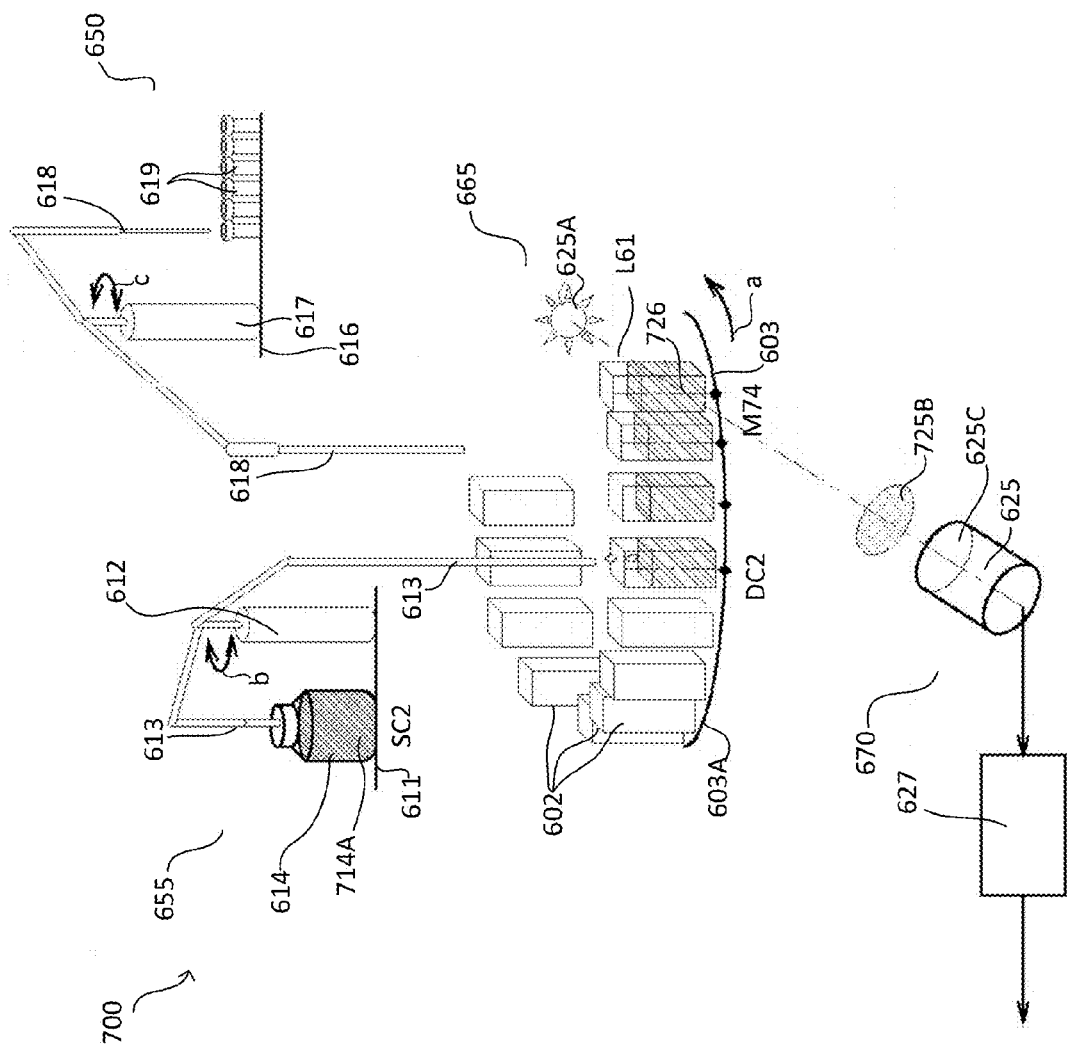
FIGS. 7A-7B show various embodiments of a validation method to verify the accuracy of the light path length of an optical analysis cell in an automated analyzer.

As described above, the path length of the optical analysis cell may not be fixed or constant. In view of this, the concentration of component of analysis as obtained from the automated analyzer which is calculated based on equation (2) above may not be reliable. A validation method to determine or verify the accuracy of light path length of an optical analysis cell used in an automated analyzer will now be described. FIG. 7A shows an embodiment of a validation method 700 to determine or verify the accuracy of the light path length ($L_O$) of an optical analysis cell used in an automated analyzer. As shown in FIG. 7A, the automated analyzer includes the same elements as that described in FIG. 6. For example, the automated analyzer includes a sample section 650, a reagent section 655, a reaction section 665 and an analysis section 670. As such, common features and features having the same reference numerals in FIG. 6 will not be described in detail.

In one embodiment, to determine the accuracy of the light path length of an optical analysis cell, the reagent bottle 614 is provided with a test solution 714A. The test solution 714A, for example, is a dye solution containing known molar absorptivity and concentration of a dye component. For example, the test solution 714A is a blue dye solution having absorbance maxima at 730 nm with known error (uncertainty) traceable to National Institute of Standards and Technology (NIST). Other suitable dye solution containing known molar absorptivity and concentration which is traceable to NIST or national authority may also be useful.

The validation method 700 starts by automatically dispensing a prescribed amount of test solution 714A. The test solution 714A is dispensed from the reagent bottle 614 through the reagent dispensing pipette 613 into an empty optical analysis cell 602 at the reagent discharge position. For example, when an empty optical analysis cell reaches the reagent discharge position DC2, the reagent pipette sucks and holds a prescribed amount of test solution 714A at the suction position SC2 on the reagent table 611. The prescribed amount of test solution 714A, for example, should be sufficient to allow for photometric measurement later. The reagent dispensing unit 612 then rotates the filled reagent dispensing pipette in the direction indicated by arrow b from the suction position to the discharge position. For example, when the reagent dispensing pipette reaches the reagent discharge position, it discharges the test solution into the empty optical analysis cell at the discharge position on the turntable 603. In this case, the test solution filled in the optical analysis cell forms a measurement target liquid 726.

The validation method continues by rotating the optical analysis cell which is filled with the measurement target liquid to a measuring position, such as M74. The measurement target liquid in the optical analysis cell traverses the light L61 from the light source 625A so that the colored condition of the blue dye solution is observed. Thus, optical characteristic of the measurement target liquid can be measured several times.

The light passes through the optical analysis cell which is filled with the measurement target liquid 726 and the transmitted light traverses a filter 725B. The filter 725B, for example, is a 730 nm filter and a signal having a magnitude representative of a transmitted light intensity is supplied to the converter 625C. The analog signal is then converted to a digital signal which includes the transmittance data by the converter and the digital signal is fed to the microcomputer. The absorbance value of the blue dye component at wavelength of 730 nm is calculated from the intensity of the transmitted light and this absorbance value is stored in a memory.

In one embodiment, the unknown light path length of the optical analysis cell is determined using equation (2) as shown above. To determine the unknown light path length ($L_O$) of the optical analysis cell, equation (2) is rearranged as follows:

$$L_O = \frac{A_{730}}{a_b} \quad (3)$$

where $L_O$=light path length of the optical analysis cell,
$A_{730}$=is the measured absorbance value of the blue dye solution in the optical analysis cell at wavelength of 730 nm,
$\epsilon_{730}$=molar absorptivity of the blue dye, which is a physical constant of the blue dye at wavelength 730 nm, and
C=concentration of the blue dye.

For simplicity, the product of $\epsilon_{730}C$ may be referred to as $a_b$. Since the concentration (C) and molar absorptivity of the blue dye component at wavelength of 730 nm ($\epsilon_{730}$) of the test solution 714A are constant and known while the absorbance value of the blue dye at wavelength of 730 nm ($A_{730}$) is obtained from the photometric measurement of the intensity of the transmitted light which passes through the measurement target liquid 726 in the optical analysis cell 602, the light path length ($L_O$) of the optical analysis cell can be determined based on equation (3) above. The calculated light path length data of the optical analysis cell is thus obtained and recorded accordingly in the memory of the microcomputer. The validation process continues by determining the light path length of adjacent and subsequent optical analysis cells and the calculated light path length data of these optical analysis cells are recorded and stored accordingly in the memory.

To validate or verify the accuracy of the light path length of the optical analysis cell, the light path length ($L_O$) as determined above is compared against the light path length value ($L_F$) provided by the manufacturer of the optical analysis cell or compared against the light path length value used to perform normal operation of the automated analyzer.

If the calculated light path length ($L_O$) based on the validation method above is different than the light path length value ($L_F$) used to perform normal operation of the automated analyzer, this implies that the light path length of the optical analysis cell is not fixed or constant. As such, to improve the reliability of the results obtained from the automated analyzer, the user may input or choose the calculated light path length ($L_O$) based on the validation method above prior to initiating the normal operation of the automated analyzer.

As shown in FIG. 7A, to verify or validate the accuracy of the light path length of the optical analysis cell, the reagent bottle is filled with a test solution 714A. The test solution, for example, is a blue dye solution with known molar absorptivity and concentration of the blue dye component having absorbance maxima at 730 nm. The reagent dispensing pipette then dispenses the test solution 714A in a sufficient amount into the optical analysis cell 602 to form the measurement target liquid 726 to enable photometric measurement. The sample dispensing pipette 618 and the diluent pipette 621 are not used to dispense the test solution 714A as shown in FIG. 7A.

Figure 7B:
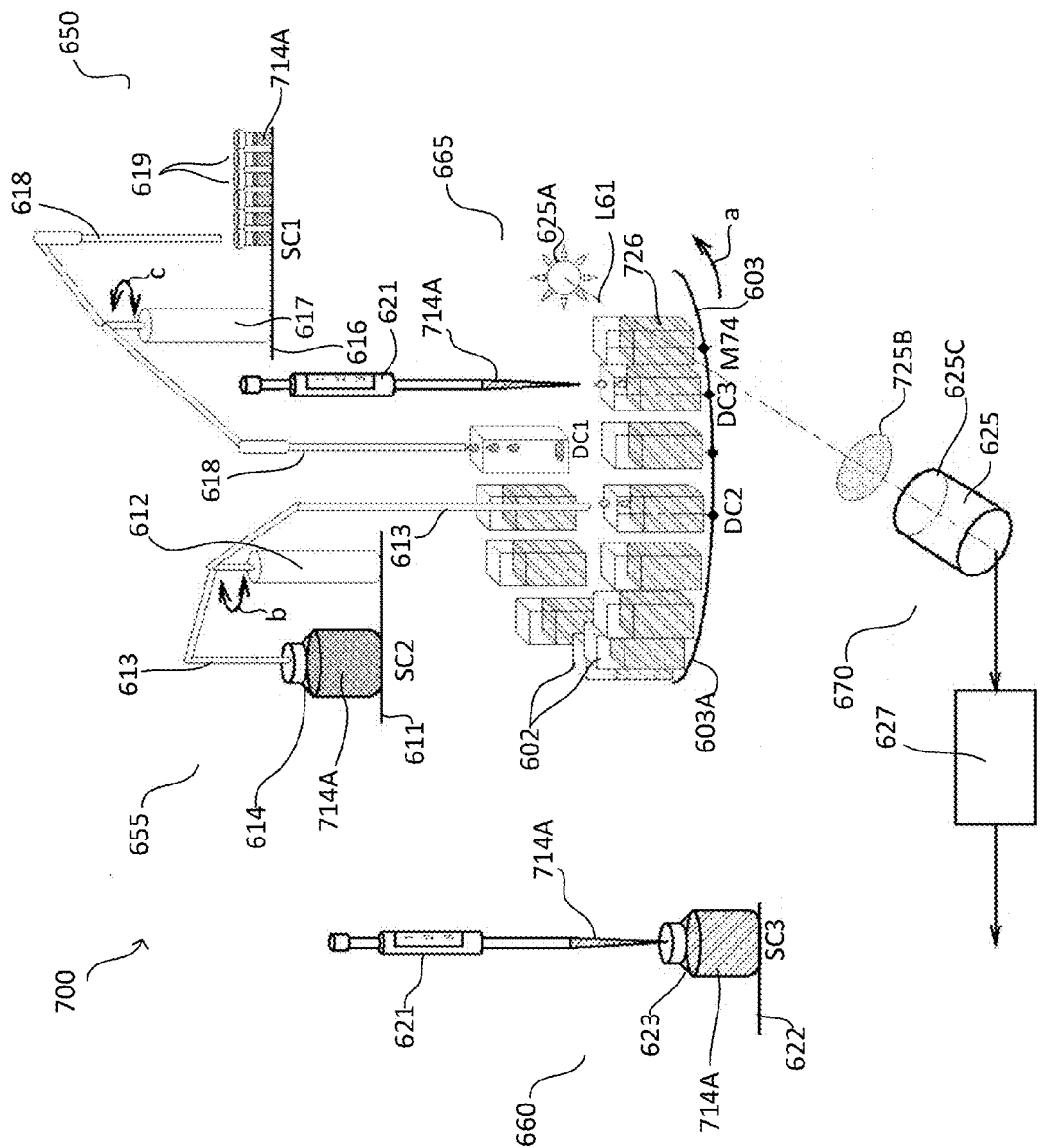

In an alternative embodiment, in the event that the dispensing capability of reagent dispensing pipette 613 is limited, the validation method 700 can be modified such that the sample bottles 619 and/or the diluent bottle 623 are filled with the test solution 714A, such as a blue dye solution containing known molar absorptivity and concentration of the blue dye component having absorbance maxima at 730 nm as shown in FIG. 7B. In such case, the sample dispensing pipette 618, the reagent dispensing pipette 613 and the diluent pipette 621 are together deployed to dispense sufficient amount of test solution 714A, such as the blue dye solution, to allow for photometric measurements to be performed.

For example, the validation method may initiate with dispensing small prescribed amount of test solution 714A from the sample dispensing pipette 618 into an empty optical analysis cell 602 at the discharge position DC1 as shown in FIG. 7B. The filled optical analysis cell then rotates to the reagent dispensing position DC2. A small prescribed amount of test solution 714A is dispensed from the reagent dispensing pipette 613 into the filled optical analysis cell at DC2. The method continues to rotate the filled optical analysis cell to a diluent discharge position DC3 of which a diluent dispensing pipette 621 is used to discharge a prescribed amount of test solution 714A. In this case, the total test solutions which are dispensed by the sample dispensing pipette, the reagent dispensing pipette and the diluent dispensing pipette in the optical analysis cell form the measurement target liquid 726 which is in sufficient amount to allow for photometric measurements. The validation method continues by rotating the optical analysis cell which is filled with the measurement target liquid to a measuring position, such as M74. The measurement target liquid in the optical analysis cell traverses the light L61 from the light source 625A so that the colored condition of the blue dye solution is observed. Thus, optical characteristic of the measurement target liquid can be measured several times and the light path length of the optical analysis cell ($L_O$) is calculated based on equation (3) as described above. To validate or verify the accuracy of the light path length of the optical analysis cell, the light path length ($L_O$) as calculated above is compared against the light path length value ($L_F$) provided by the manufacturer of the optical analysis cell or compared against the light path length value used to perform normal operation of the automated analyzer.

The validation process 700 as shown in FIG. 7B continues by determining the light path length of adjacent and subsequent optical analysis cells and the calculated light path length data of these optical analysis cells are recorded and stored accordingly in the memory.

The validation method 700 as described in FIGS. 7A and 7B offers several advantages. For example, the validation method 700 as described in FIGS. 7A and 7B is able to verify or validate the accuracy of the light path length of an optical analysis cell used in an automated analyzer. The results obtained by the validation method 700 are standardized and traceable to NIST or national authority. For instance, the parameters of the test solution having the blue dye component are traceable to NIST or national authority. In addition, the validation method 700 is relatively fast and easy to be performed.

Figure 8:
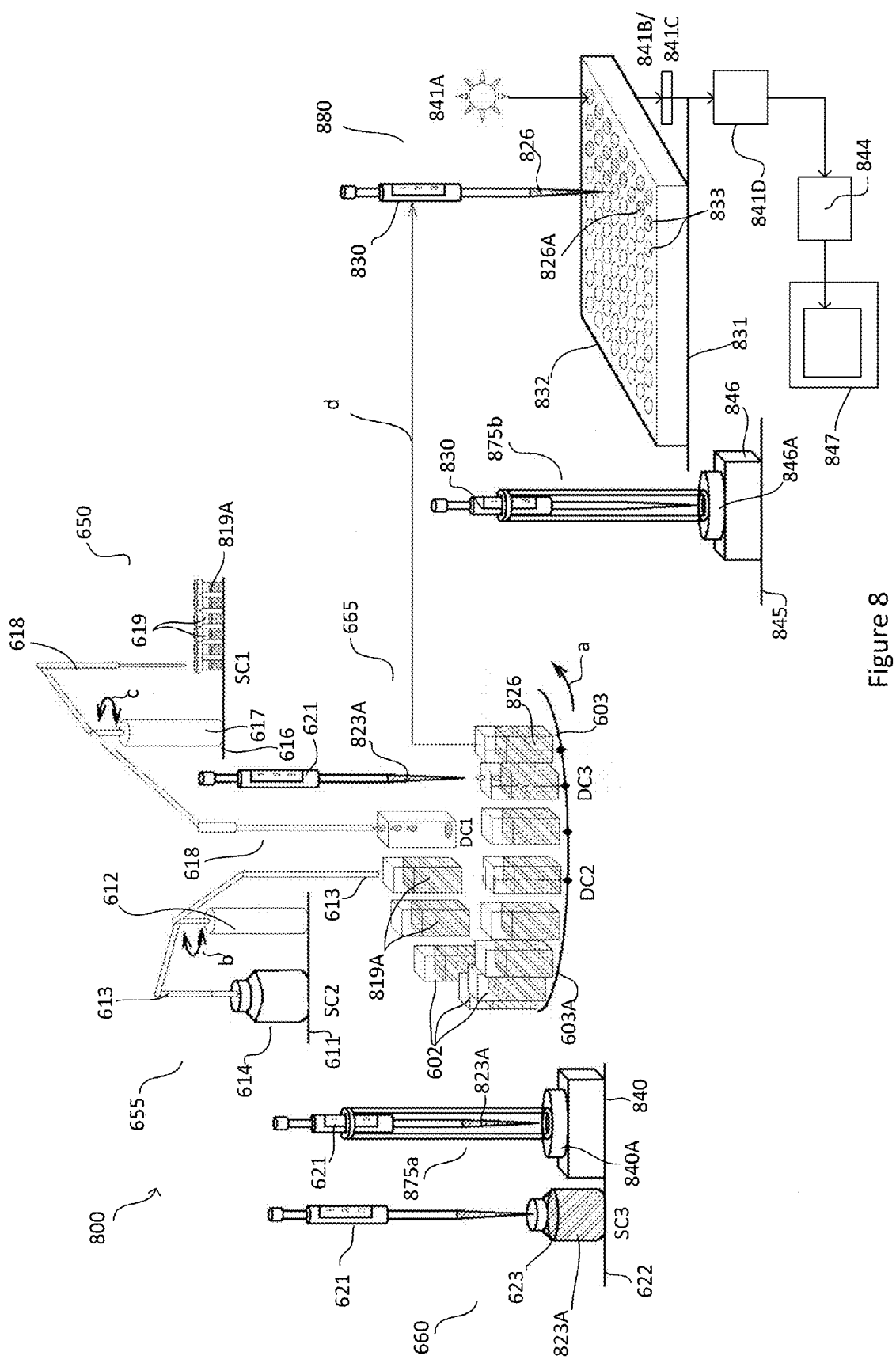
FIG. 8 shows an embodiment of a validation method to verify the accuracy of dispensed volume of a dispensing pipette under test in an automated analyzer.

As described earlier, it is also possible that the actual dispensed volume of a dispensing pipette used in an automated analyzer is above or below the amount as prescribed or defined by the user. As such, the concentration of component of analysis as obtained from the automated analyzer which is calculated based on equation (2) above may not be reliable. A validation method to determine or verify the accuracy of the dispensed volume of a dispensing pipette used in an automated analyzer will now be described. FIG. 8 shows a validation method 800 to determine or verify the accuracy of the dispensed volume of a dispensing pipette used in the automated analyzer. As shown in FIG. 8, the automated analyzer includes the same elements as that described in FIG. 6. For example, the automated analyzer includes a sample section 650, a reagent section 655, a diluent section 660, a reaction section 665 and an analysis section (not shown). As such, common features and features having the same reference numerals in FIG. 6 will not be described in detail. In one embodiment, to conduct the validation method 800, a measurement section 875 and a validation section 880 are provided. The measurement section and the validation section, in one embodiment, are provided separately from the automated analyzer. It is understood that the measurement section and validation section may be provided as part of the automated analyzer.

Referring to FIG. 8, the measurement section 875 includes first and second subsections 875a and 875b. The first measurement subsection 875a includes a weighing unit 840. As shown, the first measurement subsection 875a is provided adjacent to the diluent section 660. It is understood that the first measurement subsection may be disposed at other suitable location. The weighing unit 840 includes a weighing machine 840A for measuring, for example, the weight of the diluent dispensing pipette 621 with or without diluent. It is understood that the weighing machine 840A may also be used to measure the weight of other filled or unfilled dispensing pipette.

The validation section 880 includes a measurement microplate or an optical measurement plate system 832. The measurement microplate includes a plurality of retention grooves or wells 833. The validation section also includes a transfer pipette 830 for dispensing solution for validation purposes as will be described later. As shown in FIG. 8, the second measurement subsection 875b is provided adjacent to the validation section 880. It is understood that the second measurement subsection may also be disposed at other suitable location. The second measurement subsection 875b, for example, includes a weighing unit 846 having a weighing machine 846A for measuring, for example, the weight of the transfer pipette 830 with or without solution therein. The weighing unit 846 is disposed on a measuring table 845.

The validation method 800 to verify whether the actual dispensed volume of a dispensing pipette under test ($V_{AC}$) is the same as the volume predefined by the user ($V_U$) will now be described. In one embodiment, the actual dispensed volume of a dispensing pipette under test is determined based on a dual dye ratio method. In one embodiment, the sample dispensing pipette 618 is chosen as the dispensing pipette under test as shown in FIG. 8. To determine the accuracy of the dispensed volume of the sample dispensing pipette 618, the sample cup 619 is provided with a test solution 819A. The test solution 819A may be referred to as a first dye solution. The test solution 819A contained in the sample cup, in one embodiment, is a dye solution containing two dye components. For example, the two dye components of the test solution 819A includes a first dye component, which is a red dye component having distinct absorbance at 520 nm and a second dye component, which is a blue dye component having distinct absorbance maxima at 730 nm. In one embodiment, the molar absorptivity ($\epsilon$) and concentration (C) of the two dye components are known and include known errors (uncertainty) traceable to NIST. Other suitable dye solution having two dye components with known molar absorptivity and concentration traceable to NIST may also be useful.

The validation method 800 starts by automatically dispensing an amount of test solution 819A from the sample cup 619 through the sample dispensing pipette 618 into an empty optical analysis cell 602 at the sample discharge position. For example, when an empty optical analysis cell 602 reaches the sample discharge position DC1, the sample dispensing pipette 618 sucks and holds an amount of the test solution 819A at the suction position SC1 on the sample table 616. The amount of test solution 819A dispensed by the sample dispensing pipette at this stage is supposed to be the same as the dispensed volume of sample solution predefined by the user ($V_U$) when the automated analyzer performs its normal operation. The sample dispensing unit 617 then rotates the filled sample dispensing pipette 618 in the direction indicated by arrow c from the suction position to the discharge position DC1. For example, when the sample dispensing pipette 618 reaches the sample discharge position DC1, it discharges the test solution 819A into the empty optical analysis cell 602 at the discharge position DC1 on the turntable 603.

The amount of the test solution 819A dispensed by the sample dispensing pipette 618 into the optical analysis cell 602 may not be sufficient to allow for photometric measurements. As such, the validation process 800 continues to rotate the filled optical analysis cell to a diluent discharge position. For example, when the filled optical analysis cell reaches the diluent discharge position, such as the diluent filling position DC3, a prescribed amount of a diluent 823A is dispensed into the optical analysis cell which is filled with test solution 819A. For example, the user manually aspirates a prescribed amount of diluent 823A from a diluent bottle 623 using a diluent dispensing pipette 621 such that the total volume in the filled optical cell is at about 200 µl. Other suitable amount of diluent may also be useful so long as the total volume of the filled optical cell is sufficient for photometric measurement for validation later. In one embodiment, the diluent 823A includes a dye solution. The diluent 823A may be referred to as a second dye solution. The dye solution of the diluent 823A includes a third dye component, which is a blue dye component having distinct absorbance maxima at 730 nm with known molar absorptivity and concentration and includes known errors (uncertainty) traceable to NIST. The concentration of the blue dye component in the diluent 823A is at the same concentration as the blue dye component in the test solution 819A.

In one embodiment, the filled diluent dispensing pipette is placed on the weighing machine 840A at the first measurement subsection 875a and the weight of the filled diluent pipette is measured using gravimetric method. The weight value of the filled diluent pipette (W81) is recorded.

The user then transfers the diluent 823A to the filled optical analysis cell at the diluent discharge position DC3. Once the diluent is discharged into the filled optical analysis cell, the emptied diluent pipette 621 is put on the weighing machine 840A at the first measurement subsection 875a. The weight of the emptied diluent dispensing pipette (W82) is measured using gravimetric method and is recorded accordingly. As such, the amount of diluent injected into the optical analysis cell is determined on the basis of the weight difference of the diluent dispensing pipette 621 before and after dispensing. Further, this is also to ensure that the prescribed amount of diluent is completely dispensed into the optical analysis cell and no diluent remains in the diluent dispensing pipette 621.

The test solution 819A and diluent 823A in the optical analysis cell 602 are mixed by a mixing mechanism (not shown), such as an agitator, to form a measurement target liquid 826. The purpose of the diluent is to fill the optical analysis cell such that it has a total volume which is sufficient to allow for optical or photometric measurements.

The validation method 800 continues by rotating the optical analysis cell which is filled with the test solution and diluent to a prescribed position awaiting to be transferred to the validation section 880. In one embodiment, the validation method 800 continues by transferring the entire measurement target liquid 826 to the measurement microplate 832 for verification at the validation section 880 as shown by arrow d.

For example, the measurement target liquid 826 in the optical analysis cells 602 is removed by the user using a transfer pipette 830. The filled transfer pipette is placed on the weighing machine 846A at the second measurement subsection 875b and the weight of the filled transfer pipette is measured using gravimetric method. The weight value of the filled transfer pipette (W83) is recorded.

Using the transfer pipette 830, the user then transfers the measurement target liquid 826 to one of the plurality of retention wells 833 in the measurement microplate 832 on a validation rack 831 at the validation section 880. Once the measurement target liquid 826 is discharged into the retention well, the emptied transfer pipette is put on the weighing machine 846A at the second measurement subsection 875b. The weight of the emptied transfer pipette (W84) is measured using gravimetric method and is recorded accordingly. Thus, the amount of measurement target liquid injected into the retention well is determined on the basis of the weight difference of the transfer pipette before and after dispensing. Further, this is also to ensure that the entire measurement target liquid 826 is completely dispensed into the retention well and no measurement target liquid remains in the transfer pipette.

Figure 9:
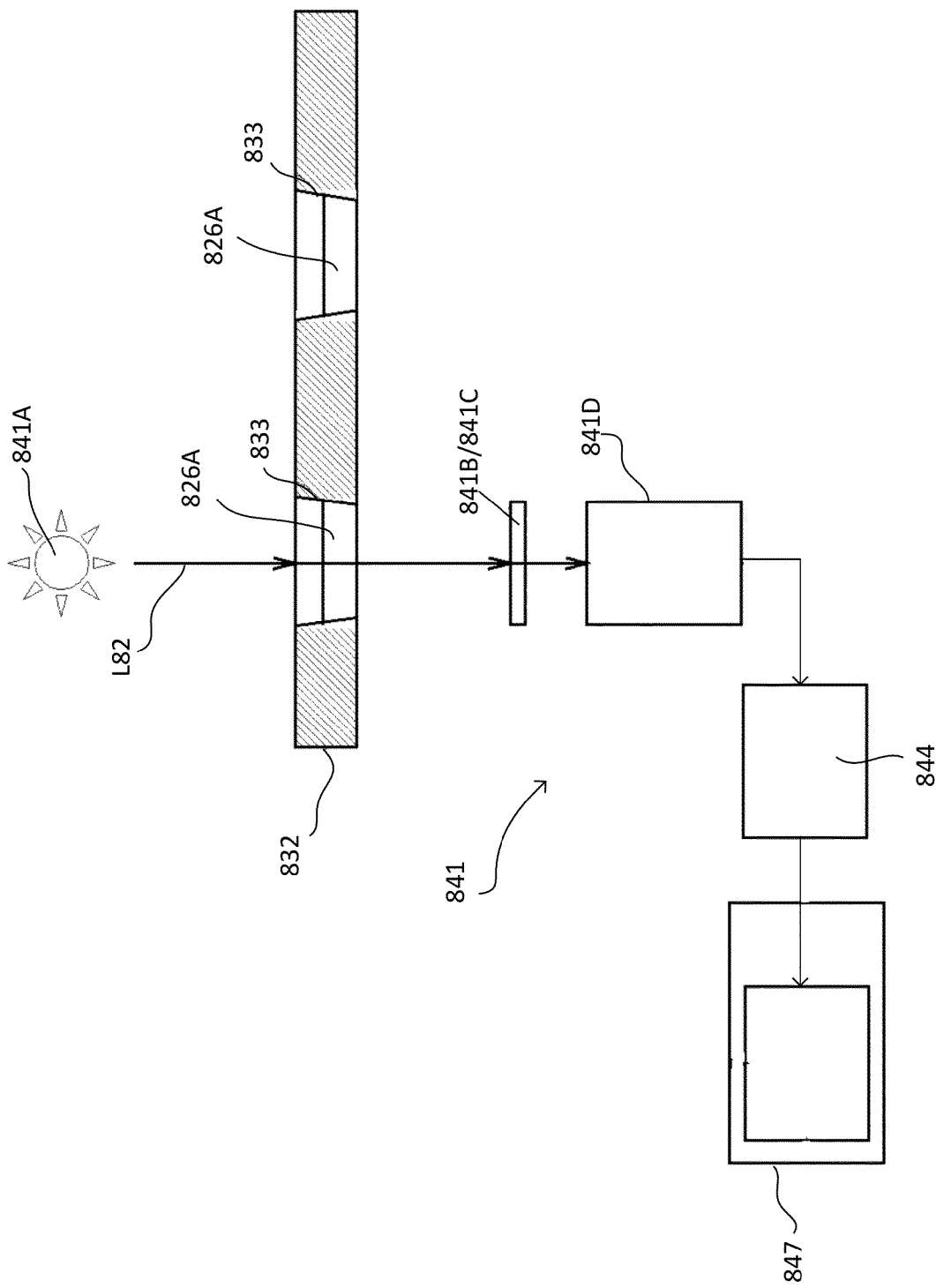
FIG. 9 shows a schematic diagram illustrating another configuration of the second optical absorbance detection unit and an optical measurement microplate.

The validation process 800 continues by measuring absorbance of the red and blue dye components in the measurement target transfer liquid 826A placed in the retention well 833 using a second optical absorbance detection unit 841 as shown in FIGS. 8 and 9.

Referring to FIG. 9, the optical absorbance detection unit 841 has a white light source 841A that emits a white light L82. The light L82 passes through the retention well 833 which is filled with the measurement target liquid 826A having red and blue dye components in a vertical direction. The transmitted light traverses a first filter 841B which allows the wavelength of 730 nm necessary for the blue dye component and a first analog signal having a magnitude representative of a transmitted light intensity of the blue dye component is supplied to a converter 841D. The analog signal is then converted to a first digital signal which includes the transmittance data of the blue dye component by the converter and the digital signal is fed to a processing unit 844 having a microcomputer. The absorbance value of the blue dye component ($A_{730}$) in the measurement target liquid 826A in the retention well is calculated from the measured transmittance data and this absorbance value is stored in a memory. Then, the first filter 841B is replaced with a second filter 841C which allows the wavelength of 520 nm necessary for the red dye component. The light passes through the retention well 833 which is filled with the red and blue dye components and the transmitted light traverses a second filter 841C and a second analog signal having a magnitude representative of a transmitted light intensity of the red dye component is supplied to the converter 841D. The analog signal is then converted to a second digital signal which includes the transmittance data of the red dye component by the converter and the digital signal is fed to the processing unit 844. The absorbance value of the red dye component ($A_{520}$) in the measurement target liquid 826A in the retention well is calculated from the measured transmittance data and this absorbance value is stored in a memory.

Thus, the absorbance values of the red and blue dye components are measured for the measurement target liquid 826A in the retention well 833 at both wavelengths. These absorbance values collected from the retention well in the microplate are used to calculate the actual dispensed volume ($V_{AC}$) of the dispensing pipette under test, which is the sample dispensing pipette 618 in this embodiment.

FIGS. 10A-10C shows the determination of the actual dispensed volume ($V_{AC}$) of the sample dispensing pipette 618. For illustration purpose, the geometric shape of the retention wells 833 in the microplate 832 is shown as a truncated cone shape. To ensure that the calculation of the actual dispensed volume of the sample dispensing pipette is accurate, every retention well in the microplate is measured with a coordinate measuring machine and a photometer to determine the mean bottom diameter (D) and mean taper angle ($\theta$) of the sidewall of each of the wells as shown in FIG. 10A. The geometric dimensions of each of the retention wells are encoded in a bar code affixed to the microplate. These geometric dimensions will be used to calculate the actual dispensed volume of the sample dispensing pipette.

The calculation of the liquid depth ($L_G$) in the retention well 833 will now be described. As described earlier, the concentration of the blue dye component in the diluent 823 is the same as the concentration of the blue dye component in the test solution 819A. Therefore, equation (3) as described above can be used to calculate the liquid depth in the retention well, which is equivalent to path length of light which passed through the measurement target liquid 826A in the retention well 833 as shown in FIG. 10B. The liquid depth ($L_G$) can be determined by the following equation (4):

$$L_G = \frac{A_{730}}{a_b} \tag{4}$$

where $L_G$=liquid depth in the retention well which is equivalent of light path length which passes through the measurement target liquid 826A in the retention well, $A_{730}$=absorbance value of the blue dye component in the measurement target liquid 826A at wavelength of 730 nm measured by the second optical absorbance detection unit 841, $a_b$=absorption per unit path length of the blue dye component at 730 nm, which is the product of ($\epsilon_{730}C$), where $\epsilon_{730}$ is the molar absorptivity of the blue dye component, which is a physical constant of the blue dye at wavelength 730 nm, and C is the concentration of the blue dye component of the test solution or diluent.

Since the concentration (C) and molar absorptivity of the blue dye component at wavelength of 730 nm of the test solution 819A or diluent 823A are known while the absorbance value of the blue dye component at wavelength of 730 nm ($A_{730}$) is obtained from the photometric measurement of the intensity of the transmitted light passes through the measurement target liquid 826A in the retention well, the light path length ($L_G$) can be determined.

Once the liquid depth ($L_G$) is determined, the geometrical equation for the volume of the truncated cone can be used to determine the total volume of measurement target liquid ($V_{TG}$) in the retention well 833. The calculation of the total volume of measurement target liquid in the retention well ($V_{TG}$) is based on the liquid depth ($L_G$) as determined from equation (4) and the geometric dimensions of the retention well 833 of the microplate, as shown in equation (5) below:

$$V_{TG} = \pi L_G \frac{D^2}{4} + \pi D L_G^2 \frac{\tan(\theta)}{2} + \pi L_G^3 \frac{\tan^2(\theta)}{3} \tag{5}$$

With the calculated total volume of measurement target liquid in the retention well ($V_{TG}$) above, the actual dispensed volume ($V_{AC}$) of the dispensing pipette under test, which is the sample dispensing pipette in this case, can be determined based on equation (6), which is similar to equation (1), as shown below:

$$V_{AC} = V_{TG} \left(\frac{a_b}{a_r}\right)\left(\frac{A_{520}}{A_{730}}\right) \tag{6}$$

where $V_{AC}$=the actual dispensed volume of the dispensing pipette under test, $V_{TG}$=total volume of measurement target liquid 826A in the retention well as calculated based on equation (5) above, $a_b$=absorption per unit path length of the blue dye component at 730 nm, which is the product of ($\epsilon_{730}C$), $a_r$=absorption per unit path length of the red dye component at 520 nm, which is the product of ($\epsilon_{520}C$), where $\epsilon_{520}$ is the molar absorptivity of the red dye component, which is a physical constant of the red dye at wavelength 520 nm, and C is the concentration of the red dye component of the test solution, $A_{730}$=absorbance value of the blue dye component at wavelength of 730 nm measured by the second optical absorbance detection unit 841, and $A_{520}$=absorbance value of the red dye component at wavelength of 520 nm measured by the second optical absorbance detection unit 841.

The concentration (C) and molar absorptivity ($\epsilon_{730}$) of the blue dye component at wavelength of 730 nm of the test solution 819A or diluent 823A as well as the concentration (C) and the molar absorptivity ($\epsilon_{520}$) of the red dye component at the wavelength of 520 nm of the test solution 819A are known. On the other hand, the absorbance value of the blue dye component at wavelength of 730 nm ($A_{730}$) and the absorbance value of the red dye component at wavelength of 520 nm are obtained from the photometric measurement of the intensity of the transmitted light passes through the measurement target liquid 826A in the retention well 833. Since all these values are known and the $V_{TG}$ is obtained from the calculation based on equation (5), the actual dispensed volume ($V_{AC}$) of a dispensing pipette under test can be determined and is transmitted to a validation result processing unit 847.

To validate or verify the accuracy of the dispensed volume of the sample dispensing pipette 618, the actual dispensed volume ($V_{AC}$) as determined above is compared against the volume predefined by the user ($V_U$). If the calculated actual dispensed volume ($V_{AC}$) based on the validation method 800 above is different than the dispensing volume of the sample dispensing pipette predefined by the user ($V_U$) for normal operation of the automated analyzer, this implies that the sample dispensing pipette 618 does not accurately or precisely dispense the amount of sample solution as predefined by the user during normal operation of the automated analyzer. As such, to improve the reliability of the results obtained from the automated analyzer, the user may need to fine tune, calibrate or adjust the sample dispense pipette accordingly prior to initiating the normal operation of the automated analyzer.

The actual dispensed volume ($V_{AC}$) as determined above can also be used to check whether the volume dispensed by the sample dispensing pipette is within a dispensing accuracy curve DT as described in FIG. 4. For example, when the result of the actual dispensed volume ($V_{AC}$) is within the area demarcated by the dispensing accuracy curve DT, the dispensing accuracy of the sample dispensing pipette of the automated analyzer is within the allowed range and the user need not fine tune or adjusts the sample dispensing pipette. On the other hand, if the actual dispensed volume ($V_{AC}$) as determined above is out of the area demarcated by the dispensing accuracy curve DT as shown in FIG. 4, the user is required to take necessary action to make further adjustment to the sample dispensing pipette.

The validation method 800 as described in FIG. 8 offers several advantages. For example, the validation method 800 as described in FIG. 8 is able to verify or validate the accuracy of the dispensed volume of any dispensing pipette in an automated analyzer. The validation method 800 is able to measure small volumes which are generally dispensed by any dispensing pipette in an automated analyzer. In addition, the results obtained by the validation method 800 are standardized and traceable to NIST or national authority. For instance, the parameters of the dye solutions and the geometric dimensions of the retention wells of the measurement microplate are properly characterized and traceable to NIST or national authority. Further, the results obtained from the validation method 800 is also highly reliable as the validation method 800 also includes measurements of the diluent dispensing pipette and the transfer pipette before and after dispensing using gravimetric method which ensure or confirm that no solution remains in these pipettes after dispensing. Moreover, the validation method 800 also allows for high swiftness and molecular level volumetric measurement to be achieved.

Figure 11:
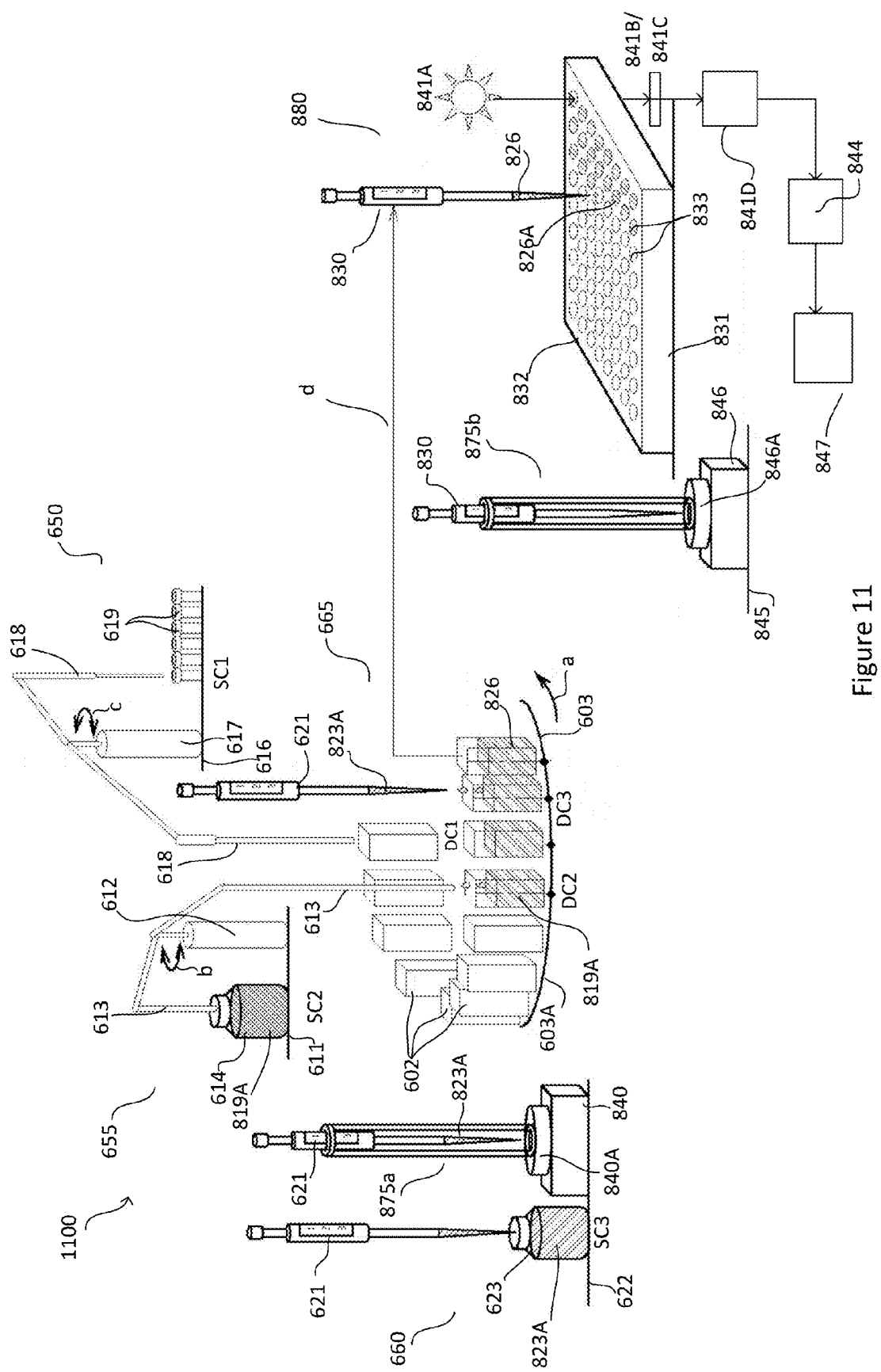
FIG. 11 shows an embodiment of a validation method to verify the accuracy of dispensed volume of another dispensing pipette under test in an automated analyzer.

As described, the validation method 800 as described in FIG. 8 is able to verify or validate the accuracy of the dispensed volume of any dispensing pipette in an automated analyzer. The validation method 800 may be modified to verify or validate the accuracy of the dispensed volume of another dispensing pipette, such as the reagent dispensing pipette. A validation method to determine or verify the accuracy of the dispensed volume of the reagent dispensing pipette 613 in an automated analyzer will now be described. FIG. 11 shows a validation method 1100 to determine or verify the accuracy of the dispensed volume of a dispensing pipette under test, which is the reagent dispensing pipette, in the automated analyzer 600 as described in FIG. 6. As shown in FIG. 11, the automated analyzer includes the same elements as that described in FIG. 8. For example, the automated analyzer includes a sample section 650, a reagent section 655, a diluent section 660, a reaction section 665 and an analysis section (not shown). To perform the validation method 1100, a measurement section 875 and a validation section 880 which are the same as that described in FIG. 8 are provided. As such, common features and features having the same reference numerals in FIG. 8 will not be described in detail.

The validation method 1100 to verify whether the actual dispensed volume of the dispensing pipette under test ($V_{AC}$) is the same as the volume predefined by the user ($V_U$) will now be described. In one embodiment, the actual dispensed volume of a dispensing pipette under test is determined based on a dual dye ratio method. In one embodiment, the dispensing pipette under test is the reagent dispensing pipette 613. To determine the accuracy of the dispensed volume of the reagent dispensing pipette 613, the reagent bottle is provided with the test solution 819A. The test solution 819A may be referred to as a first dye solution. The test solution 819A is the same as the test solution 819A described in FIG. 8. The test solution 819A contained in the reagent bottle 614, in one embodiment, is a dye solution containing two dye components. For example, the first dye component of the test solution 819A includes a red dye component having distinct absorbance at 520 nm while the second dye component of the test solution 819A includes a blue dye component having distinct absorbance maxima at 730 nm. In one embodiment, the molar absorptivity ($\epsilon$) and concentration (C) of the two dye components are known and include known errors (uncertainty) traceable to NIST. Other suitable dye solution having two dye components with known molar absorptivity and concentration traceable to NIST may also be useful.

The validation method 1100 starts by automatically dispensing an amount of test solution 819A from the reagent bottle 614 through the reagent dispensing pipette 613 into an empty optical analysis cell 602 at the reagent discharge position. For example, when an empty optical analysis cell 602 reaches the reagent discharge position DC2, the reagent dispensing pipette 613 sucks and holds an amount of the test solution 819A at the suction position SC2 on the reagent table 611. The amount of test solution 819A dispensed by the reagent dispensing pipette at this stage is supposed to be the same as the dispensed volume of reagent solution predefined by the user ($V_U$) when the automated analyzer performs its normal operation. The reagent dispensing unit 612 then rotates the filled reagent dispensing pipette 613 in the direction indicated by arrow b from the suction position to the discharge position DC2. For example, when the reagent dispensing pipette 613 reaches the reagent discharge position DC2, it discharges the test solution 819A into the empty optical analysis cell 602 at the discharge position DC2 on the turntable 603.

The amount of the test solution 819A dispensed by the reagent dispensing pipette 613 into the optical analysis cell 602 may not be sufficient to allow for photometric measurements. As such, the validation process 1100 continues to rotate the filled optical analysis cell to a diluent discharge position. For example, when the filled optical analysis cell reaches the diluent discharge position, such as the diluent filling position DC3, a prescribed amount of a diluent 823A is dispensed into the optical analysis cell which is filled with test solution 819A. For example, the user manually aspirates a prescribed amount of diluent 823A from a diluent bottle 623 using a diluent dispensing pipette 621 such that the total volume in the filled optical cell is at about 200 µl. Other suitable amount of diluent may also be useful so long as the total volume of the filled optical cell is sufficient for photometric measurement for validation later. In one embodiment, the diluent 823A includes a dye solution. The diluent 823A may be referred to as a second dye solution. The diluent 823A is the same as the diluent 823A described in FIG. 8. The dye solution of the diluent 823A includes a blue dye component having distinct absorbance maxima at 730 nm with known molar absorptivity and concentration. The concentration of the blue dye component in the diluent 823A is at the same concentration as the blue dye component in the test solution 819A.

In one embodiment, the filled diluent pipette 621 is placed on the weighing machine 840A at the first measurement subsection 875a and the weight of the filled diluent pipette is measured using gravimetric method. The weight value of the filled diluent pipette (W111) is recorded.

The user then transfers the diluent 823A to the filled optical analysis cell at the diluent discharge position DC3. Once the diluent is discharged into the filled optical analysis cell, the emptied diluent pipette 621 is put on the weighing machine 840A at the first measurement subsection 875a. The weight of the emptied diluent pipette (W112) is measured using gravimetric method and is recorded accordingly. As such, the amount of diluent injected into the optical analysis cell is determined on the basis of the weight difference of the diluent dispensing pipette before and after dispensing. Further, this is also to ensure that the prescribed amount of diluent is completely dispensed into the optical analysis cell and no diluent remains in the diluent pipette 621.

The test solution 819A and diluent 823A in the optical analysis cell 602 are mixed by a mixing mechanism (not shown), such as an agitator, to form a measurement target liquid 826. The purpose of the diluent is to fill the optical analysis cell such that it has a total volume which is sufficient to allow for optical or photometric measurements.

The validation method 800 continues by rotating the optical analysis cell which is filled with the test solution and diluent to a prescribed position awaiting to be transferred to the validation section 880. In one embodiment, the validation method 1100 continues by transferring the entire measurement target liquid 826 to the measurement microplate 832 for verification at the validation section 880 as shown by arrow d.

For example, the measurement target liquid 826 in the optical analysis cells 602 is removed by the user using a transfer pipette 830. The filled transfer pipette is placed on the weighing machine 846A at the second measurement subsection 875b and the weight of the filled transfer pipette is measured using gravimetric method. The weight value of the filled transfer pipette (W113) is recorded.

Using the transfer pipette 830, the user then transfers the measurement target liquid 826 to one of the plurality of retention wells 833 in the measurement microplate 832 on a validation rack 831 at the validation section 880. Once the measurement target liquid 826 is discharged into the retention well, the emptied transfer pipette is put on the weighing machine 846A at the second measurement subsection 875b. The weight of the emptied transfer pipette (W114) is measured using gravimetric method and is recorded accordingly. Thus, the amount of measurement target liquid injected into the retention well is determined on the basis of the weight difference of the transfer pipette before and after dispensing. Further, this is also to ensure that the entire measurement target liquid 826 is completely dispensed into the retention well and no measurement target liquid remains in the transfer pipette.

The validation process 1100 continues by measuring absorbance of the red and blue dye components in the measurement target transfer liquid 826A placed in the retention wells 833 using a second optical absorbance detection unit 841 as shown in FIG. 9. The absorbance values of the red and blue dye components are measured for the measurement target liquid 826A in the retention well 833 at both wavelengths, the same as that already described in FIG. 9. These absorbance values collected from the retention well in the microplate are used to calculate the actual dispensed volume ($V_{AC}$) of the dispensing pipette under test, which is the reagent dispensing pipette 613 in this embodiment.

The determination of the actual dispensed volume ($V_{AC}$) of the reagent dispensing pipette 613 is the same as that illustrated and described in FIGS. 10A-10C and therefore will not be described again. For example, equations (4)-(5) are used to determine the liquid depth ($L_G$) and the total volume of measurement target liquid in the retention well $V_{TG}$. With these results from these equations, the actual dispensed volume ($V_{AC}$) of the reagent dispensing pipette can be determined based on equation (6) above.

The concentration (C) and molar absorptivity ($\epsilon_{730}$) of the blue dye component at wavelength of 730 nm of the test solution 819A or diluent 823A as well as the concentration (C) and the molar absorptivity ($\epsilon_{520}$) of the red dye component at the wavelength of 520 nm of the test solution 819A are known. On the other hand, the absorbance value of the blue dye component at wavelength of 730 nm ($A_{730}$) and the absorbance value of the red dye component at wavelength of 520 nm ($A_{520}$) are obtained from the photometric measurement of the intensity of the transmitted light passes through the measurement target liquid 826A in the retention well. Since all these values are known and the $V_{TG}$ is obtained from the calculation based on equation (5), the actual dispensed volume ($V_{AC}$) of the reagent dispensing pipette 613 can be determined.

To validate or verify the accuracy of the dispensed volume of the reagent dispensing pipette 613, the actual dispensed volume ($V_{AC}$) as determined above is compared against the volume predefined by the user ($V_U$). If the calculated actual dispensed volume ($V_{AC}$) based on the validation method 1100 above is different than the dispensing volume of the reagent dispensing pipette predefined by the user ($V_U$) for normal operation of the automated analyzer, this implies that the reagent dispensing pipette 613 does not accurately or precisely dispense the amount of reagent solution as predefined by the user during normal operation of the automated analyzer. As such, to improve the reliability of the results obtained from the automated analyzer, the user may need to fine tune, calibrate or adjust the reagent dispense pipette 613 accordingly prior to initiating the normal operation of the automated analyzer.

The actual dispensed volume ($V_{AC}$) of the reagent dispensing pipette as determined above can also be used to check whether the volume dispensed by the reagent dispensing pipette is within a dispensing accuracy curve DT as described in FIG. 4. For example, when the result of the actual dispensed volume ($V_{AC}$) is within the area demarcated by the dispensing accuracy curve DT, the dispensing accuracy of the reagent dispensing pipette of the automated analyzer is within the allowed range and the user need not fine tune or adjusts the reagent dispensing pipette. On the other hand, if the actual dispensed volume ($V_{AC}$) as determined above is out of the area demarcated by the dispensing accuracy curve DT as shown in FIG. 4, the user is required to take necessary action to make further adjustment to the reagent dispensing pipette.

The validation method 1100 as described in FIG. 11 offers similar or the same advantages as that described in FIG. 8. As such, these advantages will not be described.

The validation methods 800 and 1100 as described in FIG. 8 and FIG. 11 can be used to verify the accuracy of the dispensed volume of any dispensing pipette of the automated analyzer. It is a simple and flexible method. All the user needs to do is to use the dispensing pipette under test to suck and dispense the test solution 819A and provide the diluent 823A into the optical analysis cell to form a measurement target liquid which is sufficient to allow for photometric measurement. The test solution, for example, includes first and second dye components while the diluent, for example, includes a third dye component which is at the same concentration as the second dye component of the test solution. As such, any suitable dye solutions which are standardized and traceable to NIST may be used. In addition, although the retention well is presented as having a truncated cone shape, it is understood that the well may also be in other shapes, such as but not limited to square shape. In such case, the user needs to modify equation (5) such that the geometrical equation for the volume of the square shape retention well is used to determine the total volume of measurement target liquid ($V_{TG}$) in the retention well 833.

The preferred embodiment of the invention is illustrative of the invention rather than limiting of the invention. It is to be understood that revisions and modifications may be made to methods and systems described herein while still providing a manufacturing automation system and an automated method for movement of material that fall within the scope of the included claims. All matters hitherto set forth herein or shown in the accompanying figures are to be interpreted in an illustrative and non limiting sense.

What is claimed is:

1. A method for validating the accuracy of an automated analyzer comprising:
   designating one of a plurality of dispensing pipettes of the automated analyzer as a dispensing pipette under test;
   aspirating a first dye solution having first and second dye components based on a volume predefined by a user ($V_U$) using the dispensing pipette under test into one of a plurality of optical analysis cells, wherein the first dye component absorbs light of a first wavelength while the second dye component absorbs light of a second wavelength;
   dispensing a second dye solution having a third dye component into the optical analysis cell containing the first dye solution, wherein the first and second dye solutions form a measurement target liquid;
   removing the measurement target liquid from the optical analysis cell and transferring the measurement target test liquid into one of a plurality of retention wells in a measurement microplate which is separated and independent from the optical analysis cell;
   performing photometric measurement on the same measurement target test liquid contained in the microplate to measure absorbance values of the first, second and third dye components;
   determining the actual dispense volume of the dispensing pipette under test ($V_{AC}$) based on a dual dye ratio calculation method taking into consideration the measured absorbance values; and
   validating the accuracy of the dispensing volume of the dispensing pipette under test by comparing the calculated actual dispense volume against the volume predefined by the user to determine any deviation between these two volumes.

2. The method of claim 1 wherein the third dye component absorbs light of a second wavelength.

3. The method of claim 2 wherein the first dye solution has red and blue absorption wavelength components, and the second dye solution has a blue absorption wavelength component.

4. The method of claim 2 wherein the first and second dye solutions have the same blue dye concentration.

5. The method of claim 1 wherein the dispensing pipette under test is a sample dispensing pipette of the automated analyzer.

6. The method of claim 5 wherein the first dye solution is contained in a sample cup and is aspirated from the sample cup into the optical analysis cell using the sample dispensing pipette when the sample dispensing pipette and the optical analysis cell have rotated to a prescribed first filling position on a rotatable turntable of the automated analyzer.

7. The method of claim 6 wherein the second dye solution is dispensed using a diluent dispensing pipette when the optical analysis cell containing the first dye solution has rotated to a prescribed second filling position on the rotatable turntable.

8. The method of claim 7 comprising measuring the weight of the diluent dispensing pipette which is filled with the second dye solution using a gravimetric method prior to dispensing the second dye solution into the optical analysis cell containing the first dye solution.

9. The method of claim 8 comprising measuring the weight of the diluent dispensing pipette which is emptied using a gravimetric method after dispensing the second dye solution to ensure that the second dye solution is completely dispensed into the optical analysis cell containing the first dye solution and no diluent remains in the diluent dispensing pipette.

10. The method of claim 9 wherein the measurement target liquid is removed from the optical analysis cell and is transferred into one of the plurality of retention wells in the measurement microplate using a transfer pipette.

11. The method of claim 10 comprising measuring the weight of the transfer pipette which is filled with the measurement target liquid using a gravimetric method prior to dispensing the measurement target liquid into one of the plurality of retention wells in the measurement microplate.

12. The method of claim 11 comprising measuring the weight of the transfer pipette which is emptied using a gravimetric method after dispensing the measurement target liquid to ensure that the measurement target liquid is completely dispensed into one of the plurality of retention wells.

13. The method of claim 1 wherein the dispensing pipette under test is a reagent dispensing pipette of the automated analyzer.

14. The method of claim 13 wherein the first dye solution is contained in a reagent bottle and is aspirated from the reagent bottle into the optical analysis cell using the reagent dispensing pipette when the reagent dispensing pipette and the optical analysis cell have rotated to a prescribed first filling position on a rotatable turntable of the automated analyzer.

15. The method of claim 14 wherein the second dye solution is dispensed using a diluent dispensing pipette when the optical analysis cell containing the first dye solution has rotated to a prescribed second filling position on the rotatable turntable.

16. The method of claim 15 comprising measuring the weight of the diluent dispensing pipette which is filled with the second dye solution using a gravimetric method prior to dispensing the second dye solution into the optical analysis cell containing the first dye solution.

17. The method of claim 16 comprising measuring the weight of the diluent dispensing pipette which is emptied using a gravimetric method after dispensing the second dye solution to ensure that the second dye solution is completely dispensed into the optical analysis cell containing the first dye solution and no diluent remains in the diluent dispensing pipette.

18. The method of claim 17 wherein the measurement target liquid is removed from the optical analysis cell and is transferred into one of the plurality of retention wells in the measurement microplate using a transfer pipette.

19. A method for validating the accuracy of an automated analyzer comprising:
designating one of a plurality of optical cells of the automated analyzer as an optical analysis cell under test;
aspirating a prescribed amount of test solution having a dye component using a dispensing pipette of the automated analyzer into the optical analysis cell under test, wherein the dye component absorbs light of a wavelength and has known molar absorptivity and concentration;
performing photometric measurement on the test solution contained in the optical analysis cell under test to measure absorbance value of the dye component in the test solution;
determining the actual light path length of the optical analysis cell under test taking into consideration the measured absorbance value, the known molar absorptivity and concentration of the dye component; and
validating the accuracy of the light path length of the optical analysis cell under test by comparing the calculated actual light path length against a light path length provided by manufacturer of the optical analysis cell to determine any deviation between these two lengths.

20. The method of claim 19 wherein the dye component has a blue absorption wavelength component.

* * * * *